US011526508B1

(12) United States Patent
McCallie, Jr. et al.

(10) Patent No.: US 11,526,508 B1
(45) Date of Patent: Dec. 13, 2022

(54) CONCEPT EMBEDDINGS FOR IMPROVED SEARCH

(71) Applicant: CERNER INNOVATION, INC., Kansas City, KS (US)

(72) Inventors: David P. McCallie, Jr., Stilwell, KS (US); Margaret Cushing Kolm, Kansas City, MO (US); Christopher S. Finn, Liberty, MO (US)

(73) Assignee: Cerner Innovation, Inc., Kansas City, MO (US)

( * ) Notice: Subject to any disclaimer, the term of this patent is extended or adjusted under 35 U.S.C. 154(b) by 68 days.

(21) Appl. No.: 16/913,637

(22) Filed: Jun. 26, 2020

Related U.S. Application Data

(60) Provisional application No. 62/868,195, filed on Jun. 28, 2019.

(51) Int. Cl.
*G06F 16/2452* (2019.01)
*G06F 40/279* (2020.01)
*G06F 16/248* (2019.01)
*G06N 3/08* (2006.01)
*G16H 70/20* (2018.01)

(52) U.S. Cl.
CPC ...... *G06F 16/24522* (2019.01); *G06F 16/248* (2019.01); *G06F 40/279* (2020.01); *G06N 3/08* (2013.01); *G16H 70/20* (2018.01)

(58) Field of Classification Search
CPC ............. G06F 16/24522; G06F 40/279; G06F 16/248; G06F 40/274; G06F 40/35; G06N 3/08; G16H 70/20; G10L 15/26; G10L 15/34; G10L 17/22; G10L 19/018
See application file for complete search history.

(56) References Cited

U.S. PATENT DOCUMENTS

| 10,671,942 | B1* | 6/2020 | McGovern | G06N 20/00 |
| 2004/0039599 | A1* | 2/2004 | Fralic | G06Q 40/08 |
| | | | | 705/2 |
| 2010/0049770 | A1* | 2/2010 | Ismalon | G06F 16/3325 |
| | | | | 707/765 |
| 2019/0213167 | A1* | 7/2019 | Bettencourt da Silva | |
| | | | | G06F 40/30 |
| 2019/0392082 | A1* | 12/2019 | Bell | G06N 3/08 |

* cited by examiner

*Primary Examiner* — William B Partridge
*Assistant Examiner* — Aryan D Toughiry
(74) *Attorney, Agent, or Firm* — Shook, Hardy & Bacon LLP

(57) ABSTRACT

In some examples, a word embedding is received. A word embedding includes a plurality of vectors in vector space. Each vector of the plurality of vectors represents a natural language word or other character sequence. Each vector is oriented in vector space based on a semantic similarity between each of the natural language word or other character sequence. A first distance is determined between a first vector and a second vector. A second distance is determined between a third vector and the second vector. Based at least in part on the first distance between the first vector and the second vector and the second distance between the third vector and the second vector, the third vector is moved closer or further away from the second vector. The moving is indicative of introducing a bias or removing a bias between the third vector and the second vector. This introducing or removing of bias supports more accurate and inclusive results from an application such as search of healthcare data, among other things.

20 Claims, 11 Drawing Sheets

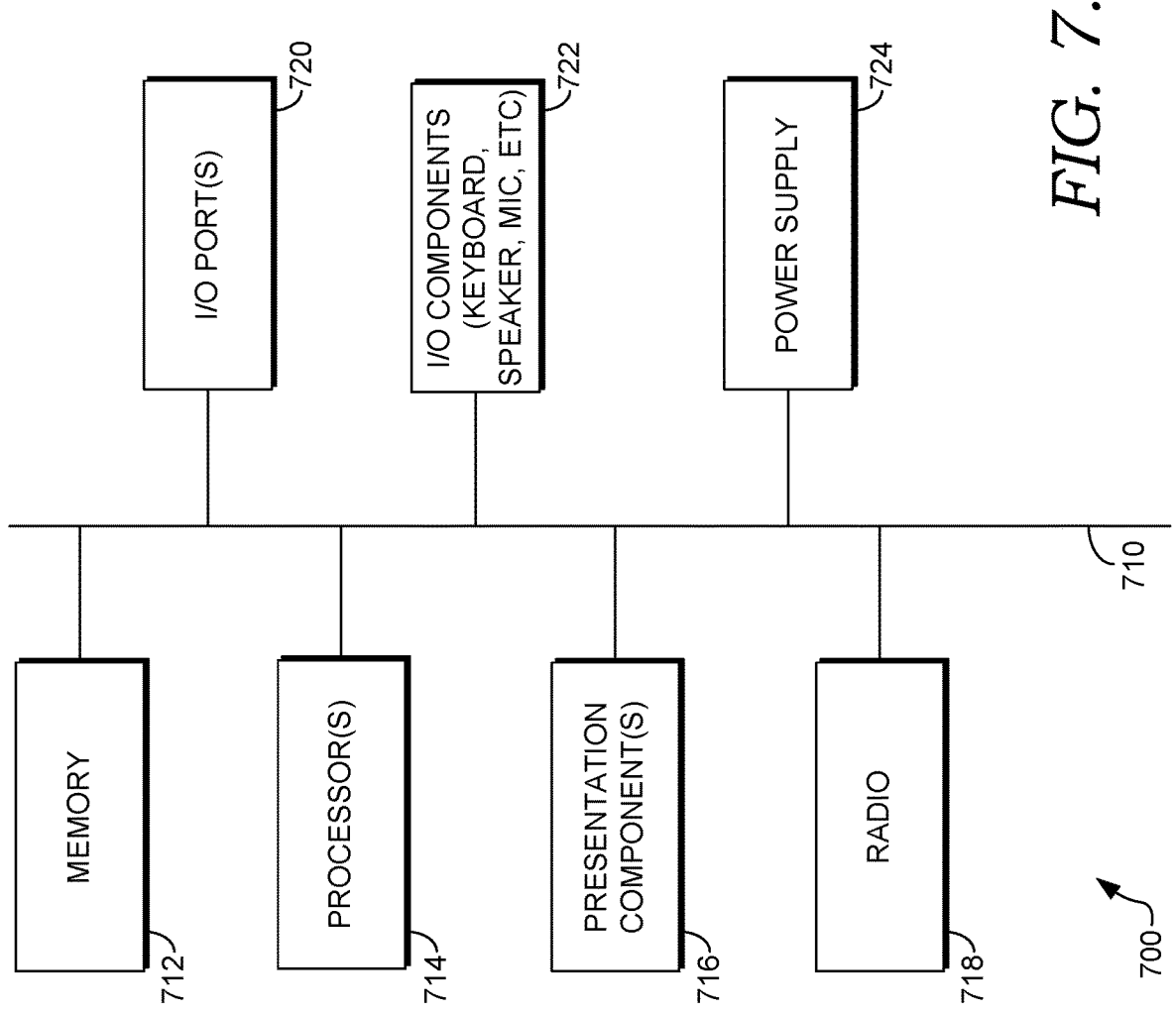

CONCEPT EMBEDDINGS FOR IMPROVED SEARCH

CROSS-REFERENCE TO RELATED APPLICATIONS

This application is a claims priority to U.S. Provisional Patent Application 62/868,195, entitled "Clinical Concept Embeddings For Improved Search" filed Jun. 28, 2019, the entirety of which is hereby incorporated by reference.

BACKGROUND

Users of computing systems rely on efficient information retrieval technologies, such as search engines. However, some information rendered by these technologies contain inherent and unwanted biases or some technologies do not bias information enough. For example, some neural networks generate a seemingly identical set of vectors that are at an unequal distance from a related vector in an embedding. This can indicate a bias and have unwanted consequences in, for example, search engine applications where patients issue queries to determine drug treatments options for a particular health condition. Instead of a search result page displaying generic drug search results or ranking them high on a results page, the search result page may instead only display the equivalent brand drug search results or rank them a lot higher on the search result page than the generic drug search results. Consequently, this may have the unwanted effect of users purchasing the more expensive brand drugs in much more frequency than generic drugs even though they may be identical in essentially every other respect.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present disclosure relate to computer-implemented methods, computer storage media, and systems that can move vectors in word embeddings, which is indicative of introducing bias or removing bias associated with the vectors. In some examples, a word embedding is received. A word embedding includes a plurality of vectors in vector space. Each vector of the plurality of vectors represents a natural language word or other character sequence. Each vector is oriented in vector space based on a semantic similarity between each of the natural language word or other character sequence. A first distance is determined between a first vector and a second vector. A second distance is determined between a third vector and the second vector. Based at least in part on the first distance between the first vector and the second vector and the second distance between the third vector and the second vector, the third vector is moved closer or further away from the second vector. The moving is indicative of introducing a bias or removing a bias between the third vector and the second vector.

Figure 5A:
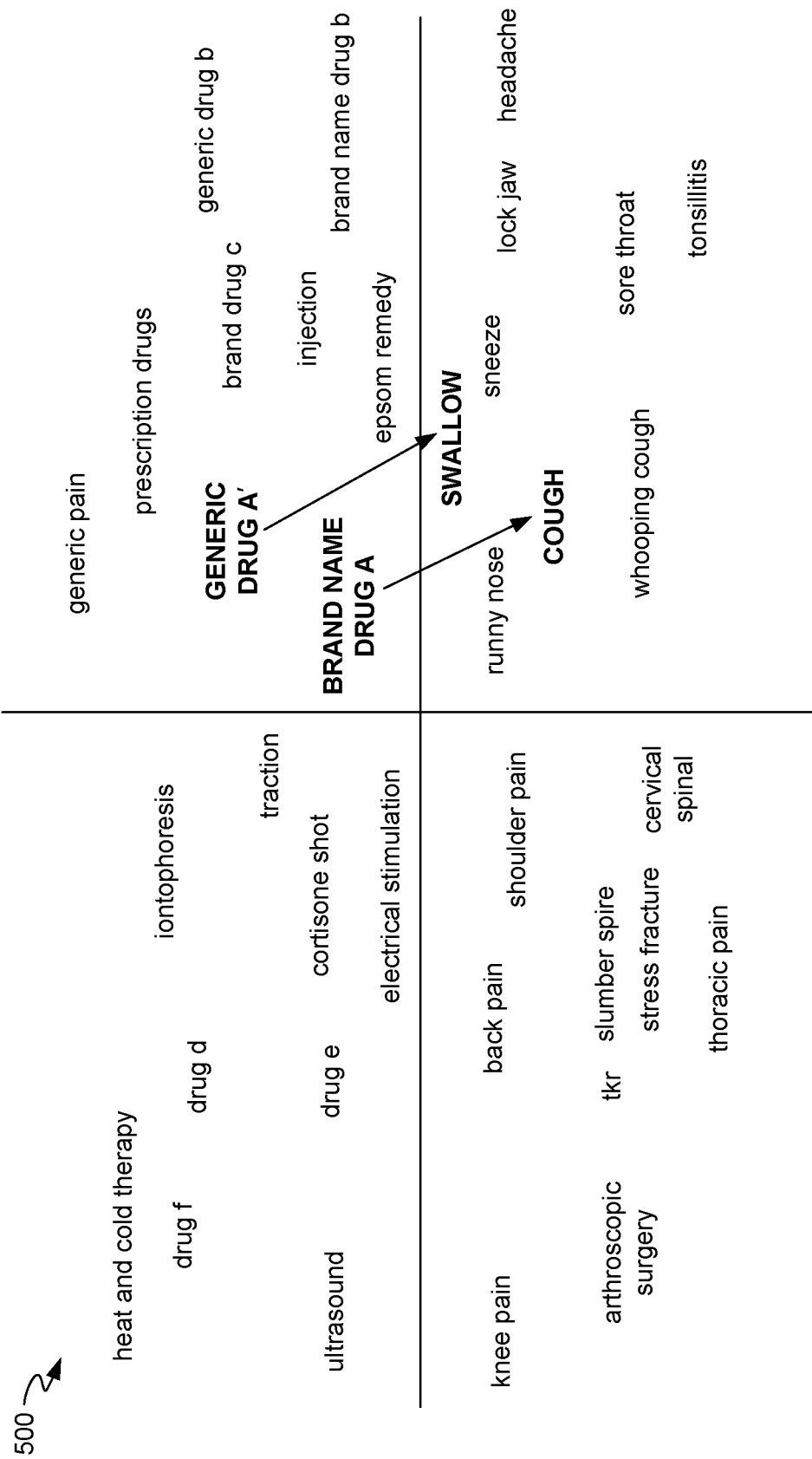
FIG. 5A is a schematic diagram illustrating how vectors associated with words are run through a word embedding vector model that outputs a word embedding, according to particular embodiments of the present invention.
Figure 5B:
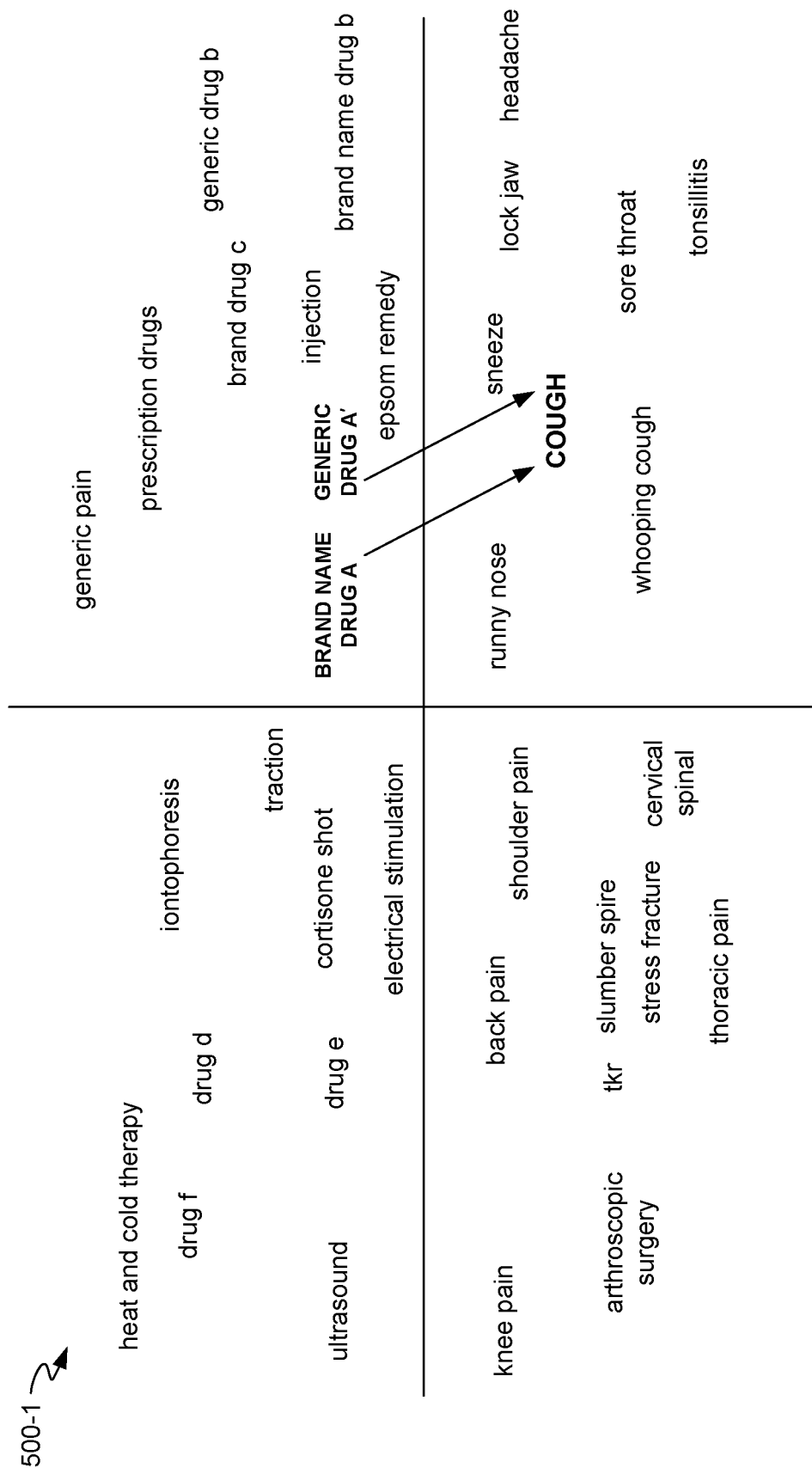
Figure 5C:
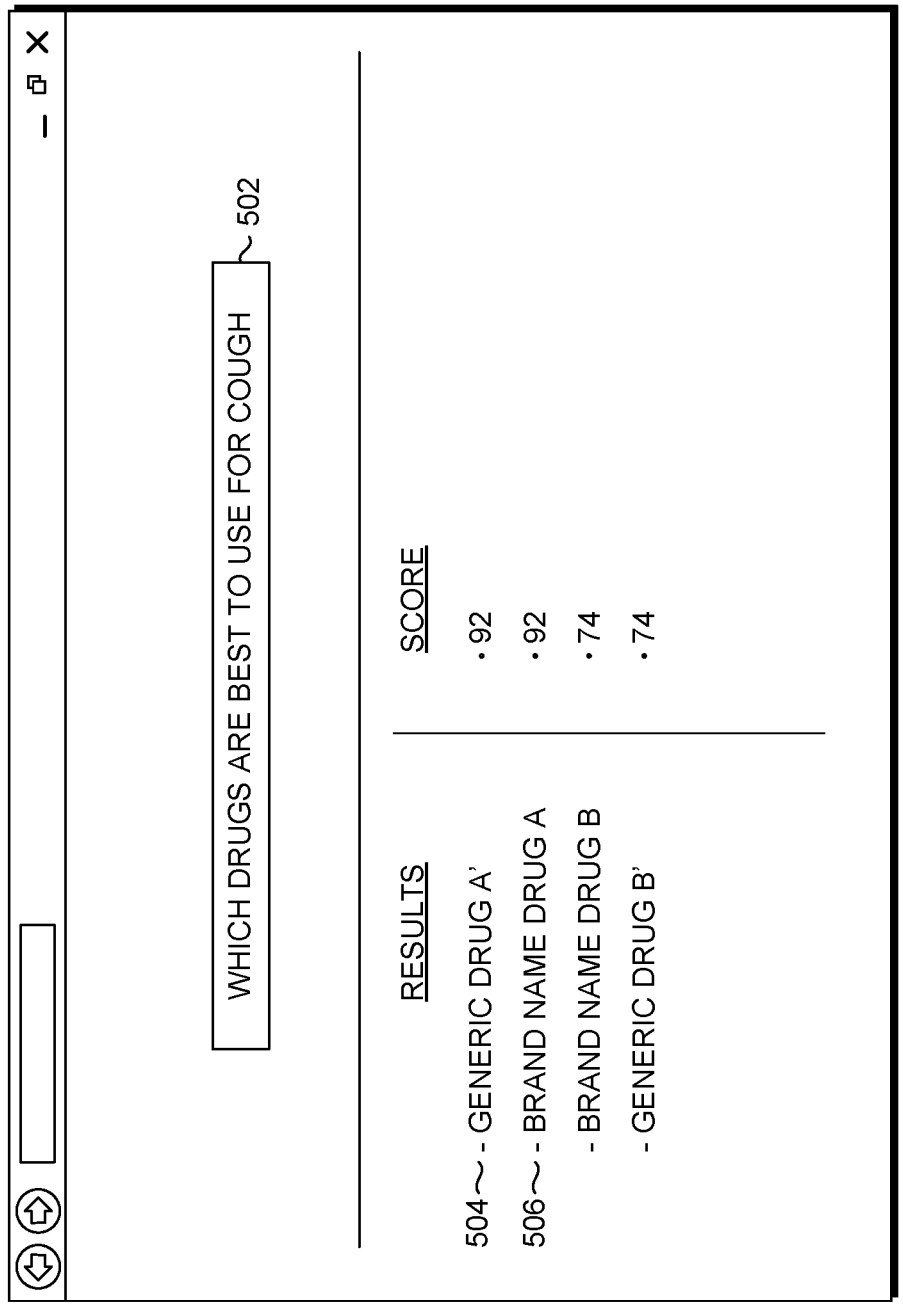
Figure 6:
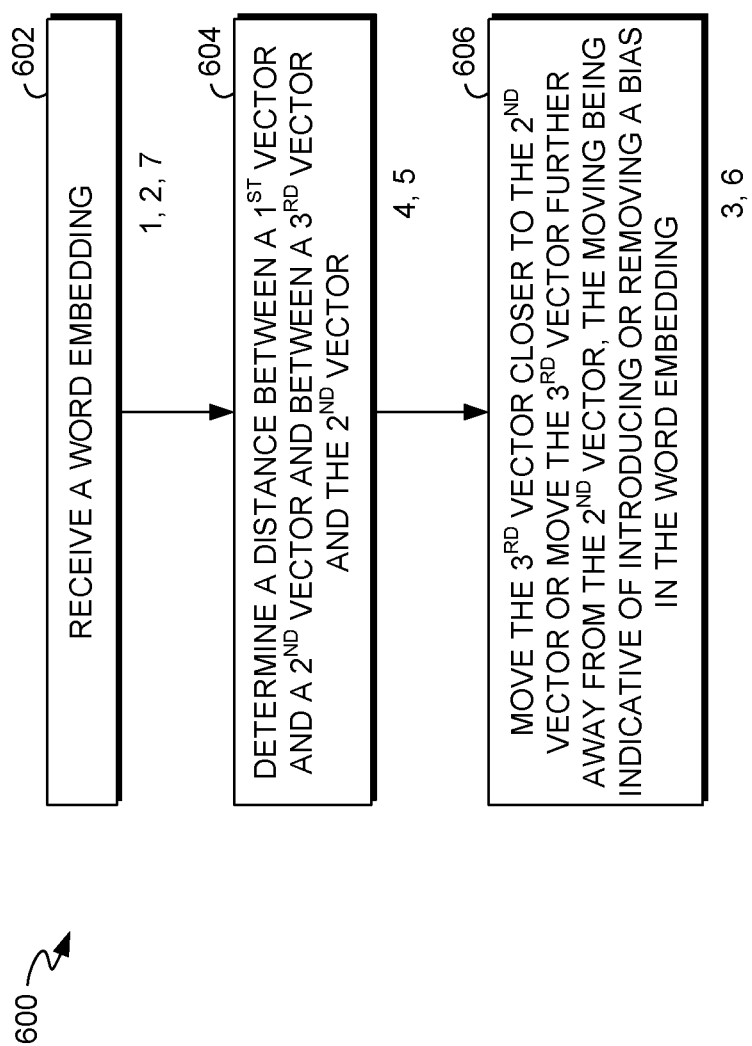

5B is a schematic diagram illustrating how vectors are moved to remove the bias indicated in FIG. 5A, according to particular embodiments of the present invention;

FIG. 5C is a screenshot of a graphical user interface that uses FIG. 5B as input, according to particular embodiments of the present invention;

FIG. 6 is a flow diagram of an example process for introducing and/or removing bias between vectors, according to particular embodiments of the present invention;

FIG. 7 is a block diagram of a computing device for use in implementing particular embodiments of the present invention.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Various embodiments of the present disclosure bias vectors and/or remove bias between vectors in word embeddings. A "vector" (also referred to as a "feature vector") as described herein includes one or more real numbers (e.g., a series of floating values or integers (e.g., [0, 1, 0, 0,])), that represent or are converted from a natural language (e.g., English) word or other character sequence (e.g., phrase, sentence, etc.). A "word embedding" (also referred to as an "embedding") as described herein represents vectors in vector space (e.g., linear space) based on a contextual (e.g., semantic) similarity, feature similarity, and/or other similarity (e.g., amount of user interaction, such as clicks) between each vector or the natural language sequence the vector represents. In some embodiments, two or more vectors that are semantically similar (e.g., have the same or similar meaning) may be mapped or embedded near each other in vector space regardless of the syntactic similarity (e.g., similarity between word structure or appearance). For example, brand A drug may be represented as close in vector space to its equivalent generic version even if they have two different names because the vectors may contain similar values that can be added, subtracted, multiplied, or otherwise linearly combined with other vectors in vector space. For instance, brand A drug may contain the same or similar chemicals as the generic version and each chemical can represent a feature or set of integers in a vector that are linearly combined for orientation in vector space, thereby making these two vectors close. Various word embedding vector models and/or neural networks use word embeddings. For example, a word embedding vector model can be or include Word2Vec, Glove, fastText, Brown Clustering, Gensim, etc. In particular embodiments, where all of the vectors represent healthcare terms, the word embedding are referred to herein as a "concept embedding."

Vector differences between words or other character sequences in word embeddings represent relationships between the words. For example, given an analogy "man is to king as woman is to x" (denoted as man; king::woman:x), arithmetic mechanisms of the word embedding find that x=queen is the best answer because queen is the same distance (or magnitude) and direction from woman as king is to man. This may take into account spatial characteristics, such as magnitude and/or directional differences between vectors. The analogies generated from these word embeddings, however, can indicate bias implicit in the data on which they were trained. Additionally, there may not be enough bias in the data for certain specific applications. This is because word embeddings are trained using second-order methods which require large amounts of data to extract associations and relationships about words. That is, the output of a prediction or classification of the word embedding depends on the training data used, which may contain biases or not enough bias. For example, the training data may indicate that for health condition Y, 90% of people used medication Z, which may be a popular brand drug, and only 10% of people used medication T, which may be a generic version of the same drug. The drugs may be similar in every respect. Accordingly, medication Z may be much closer in distance to health condition Y relative to medication T's distance to health condition Y because the training data heavily favors medication Z. However, in poverty-stricken communities, for example, it may be more desirable to take the generic drug. Thus there may be bias.

Various embodiments of the present disclosure bias vectors. It can be determined that first vector is at a same distance or closer, in vector space, to a second vector relative to a third vector's distance to the second vector. For example, using the illustration above, the system can determine that the vector representing medication Z is at the same distance or closer (e.g., using cosine distance) to a vector representing health condition Y relative to medication T's distance to health condition Y. However, the specific type of information retrieval system may be a search engine where the users are poverty stricken or are otherwise in need of generic drugs. Accordingly, any queries in this type of system should generate high-ranking search results that identify generic drugs.

Based at least in part on the first vector being at the same distance or closer, in the vector space, to the second vector, the third vector may be moved closer to the second vector such that the third vector is closer to the second vector relative to the first vector's distance to the second vector. The moving may be indicative of introducing a bias between the third vector and the second vector. For example, using the illustration above, medication T (the generic) can be moved closer to health condition Y such that medication T is closer to health condition Y relative to medication Z's new distance to health condition Y. In various embodiments, the moving includes changing a magnitude and/or direction of placement of the third vector in vector space. In some embodiments, the "moving" of vectors and the "closeness" of vectors as described herein is not a graphical illustration of moving vectors, but rather is indicative of changing a score or value for a vector where the score is closer in value to another score of another vector, etc. (e.g., via cosine distance). Accordingly, the "moving" of a vector can include generating a new score where the new score is "closer" or indicative of being close to another vector compared to a score for the same vector (and/or different vector) generated prior to the generation of the new score.

In some embodiments, the system can additionally or alternatively capture bias and remove the bias. In particular embodiments, the system can determine a first distance between a first vector and a second vector and determine a second distance between a third vector and the second vector. In some instances, the first vector is closer to the second vector relative to the third vector's distance to the second vector, indicating a bias. For example, using the illustration above, medication Z (brand drug) may be much closer to health condition Y than medication T (generic drug) is. Accordingly, in some embodiments, the third vector is scored or moved at an equal or substantially equal distance (e.g., cosine distance) to the second vector relative to the first vector's distance to the second vector. In this way, using the illustration above, the medication Z vector and the medication T vector are at a substantially similar distance away from health condition Y. Therefore, the word embedding does not indicate any bias for generic or brand drugs.

Although various examples described herein refer to specific bias categories (e.g., categories associated with drugs, treatments, or any healthcare setting category), it is understood that these are representative examples only and that word embeddings, feature vectors, or any functionality described herein can apply to different categories of bias. For instance, certain embodiments can bias and/or de-bias vectors associated with socioeconomic status, race, gender, sexual orientation, age, ethnic group, and/or the like. In an illustrative example, particular embodiments might be applied to vectors representing: words used to describe symptoms by men and by women; or symptoms by different cultural or ethnic groups; outcome assessments by age group. Additionally, the different categories of bias can be used by any suitable application outside of a healthcare setting or application, such as a banking application, a social media application, a market forecasting application, and the like.

Various categories of bias may be seen where, for example, men and women (and/or members of different racial/cultural groups) use different words to describe their identical symptoms, certain words used by certain racial/cultural groups of patients have a particular clinical meaning, and the widespread regional differences in treatment choices, unrelated to clinical science. In each of these cases, there may be words (or feature vectors representing words) used in word embeddings that are unfavorably biased (or not biased enough). Accordingly, as described in more detail herein, particular embodiments introduce bias and/or remove bias to support more accurate and inclusive results from a computer application, such as search of any healthcare-related data.

In various embodiments, the biased and/or de-biased word embedding is used for one or more computer-implemented applications. For example, in some embodiments, the system can receive, at a search engine, a query to access one or more resources (e.g., search results to respond to the query). Based on the vector distance (indicating a purposeful bias or lack of bias), the system can cause display of one or more search results to execute the query. In another example, the computer-implemented application can be a locally-installed software application that uses natural language processing or other techniques to locate or process words. In another example, the computer-implemented application can be a web application that one or more servers or computing devices (e.g., cloud nodes) use.

Existing computing systems that use embeddings or word embedding models themselves have various shortcomings. For example, existing computing systems (e.g., search engines, apps, web applications, etc.) use static word embedding models (e.g., Word2vec) to make classifications or predictions that do not employ application-specific tuning to bias results based on the context of the application. For example, a particular geriatric orthopedic care web application that practitioners use to remedy geriatric orthopedic disorders may contain search engine logic that uses standard Word2vec word embedding models. These models may not contain enough bias that reflect geriatric orthopedic care regardless of the quantity or quality of the training sessions. For example, these models may include vectors where a pediatric treatment plan is closer or the same distance to a geriatric orthopedic disorder relative to a geriatric treatment plan's distance to the same geriatric orthopedic disorder. Accordingly, these computer applications may cause inefficiencies in treatment plans and/or misdiagnosis, among other things by indicating to a clinician that the pediatric treatment plan is preferred over the geriatric treatment plan.

Various computing technologies and computer models, such as Word2Vec, are also known to exhibit biases, such as demographic discrimination, geographic discrimination, racial discrimination, gender, ads presented to users, etc. However, each of these groups use different dialects and word choices. Accordingly, languages used by groups not representative in training data are not able to be processed by natural language processing tools or other models because they are trained on "standard" data sets. Accordingly, this causes bias.

Particular embodiments of the present disclosure improve these computing technologies, such as search engines, web applications, apps, neural networks, word embedding vector models, etc. by purposefully biasing vectors and/or removing bias is in embeddings. In a search engine context, this improves search result logic in search engines because search results (e.g., which did not exist before) are generated or they are ranked higher based on introducing bias or removing bias. In other computing contexts, this improves the way the applications function because more relevant information is rendered when it is processed through a word embedding vector model. This also improves the way neural networks generate its output layer in the word embeddings since various embodiments allow this layer to be modified by introducing or removing bias in vector space.

Some existing computing systems remove bias vectors altogether from word embeddings. However, this dilutes the quality of word embeddings or causes inaccuracies in classifications or predictions. For example, some existing systems may remove a particular generic drug and brand name equivalent from a word embedding. However, both of these drugs may be the best way to remedy a particular health condition. Because these biases have been removed, the computing system may not return these results at all as remedies. Various embodiments of the present disclosure improves these technologies because they do not remove vectors that reflect bias. Rather, they move vectors in vector space while at the same time keep integrity of the model via performing functionality in a word embedding subspace and/or centering the rest of the data. In this way, each vector may be a factor in a computing application, such as search results in search engine functionality.

Figure 1:
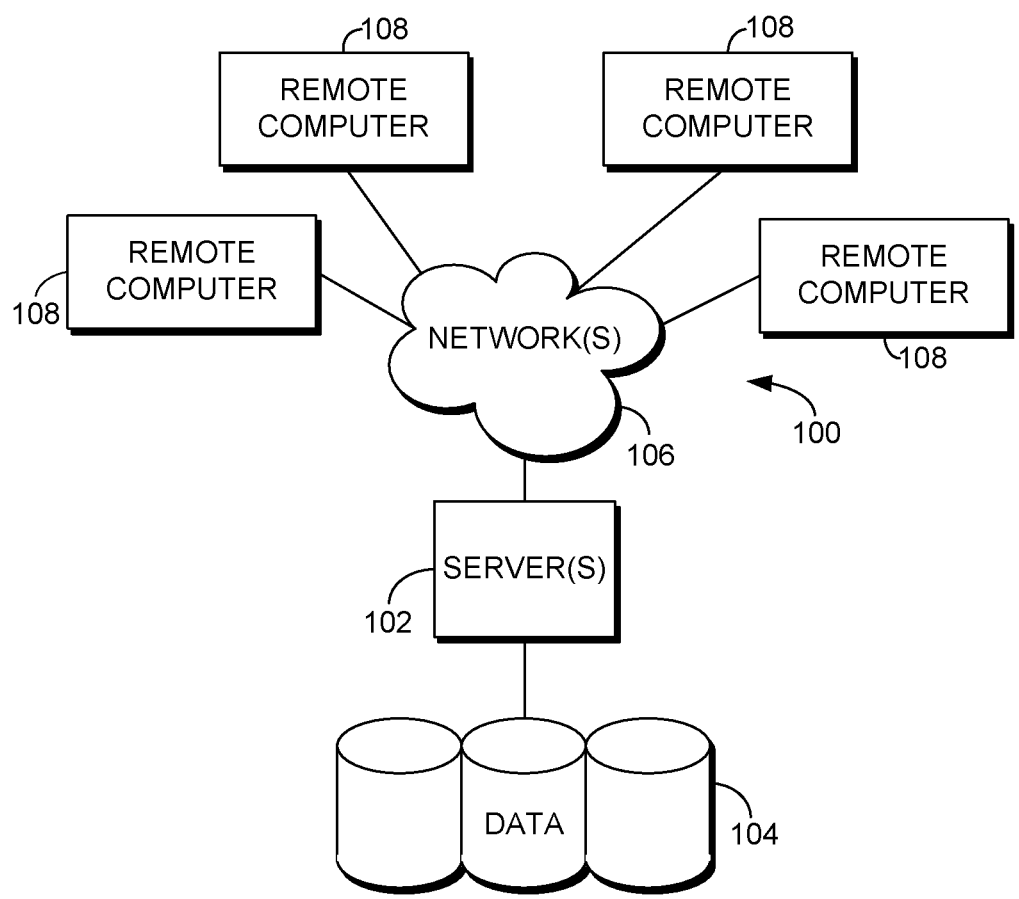
FIG. 1 is a block diagram of an example operating environment suitable to implement some embodiments of the present invention.

An exemplary computing environment 100 suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other computing system environments or configurations. Examples of well-known computing systems, environments, and/or configurations that might be suitable for use with the present invention include personal computers, server computers, hand-held or laptop devices, wearable devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises one or more computing devices in the form of server(s) 102. Exemplary components of the server(s) 102 comprise a processing unit, internal system memory, and a suitable system bus for coupling various system components, including data store 104, with the server(s) 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server(s) 102 typically includes therein, or has access to, a variety of computer-readable media. Computer-readable media can be any available media that might be accessed by server(s) 102, and includes volatile and non-volatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The server(s) 102 might operate in one or more computer networks 106 using logical connections to one or more remote computers 108. Remote computers 108 might be located at a variety of locations in a medical or research environment, including clinical laboratories (e.g., molecular diagnostic laboratories), hospitals and other inpatient settings, ambulatory settings, medical billing and financial offices, hospital administration settings, home healthcare environments, clinicians' offices, Center for Disease Control, Centers for Medicare & Medicaid Services, World Health Organization, any governing body either foreign or domestic, Health Information Exchange, and any healthcare/government regulatory bodies not otherwise mentioned. Clinicians may comprise a treating physician or physicians; specialists such as intensivists, surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer network(s) 106 comprise a local area network (LANs) and/or a wide area network (WAN). Such networking environments are commonplace in offices, enterprise-wide computer networks, intranets, and the Internet. When utilized in a WAN networking environment, the server(s) 102 might comprise a modem or other means for establishing communications over the WAN, such as the Internet. In a networking environment, program modules or portions thereof might be stored in association with the server(s) 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., server(s) 102 and remote computers 108) might be utilized.

In operation, an organization might enter commands and information into the server(s) 102 or convey the commands and information to the server(s) 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the server(s) 102. In addition to a monitor, the server(s) 102 and/or remote computers 108 might comprise other peripheral output devices, such as speakers and a printer.

Although many other internal components of the server(s) 102 and the remote computers 108 are not shown, such components and their interconnection are well known. Accordingly, additional details concerning the internal construction of the control server 102 and the remote computers 108 are not further disclosed herein, such as with respect to the computing device 700 of FIG. 7. In some embodiments, the server(s) 102 represent a stand-alone computer or computing system, such as a mainframe, blade server, and the like. Alternatively, in some embodiments, the server(s) 102 represent a set of distributed computers, such as multiple cloud computing nodes where data is provisioned or exchanged between the cloud computing nodes.

Figure 2:
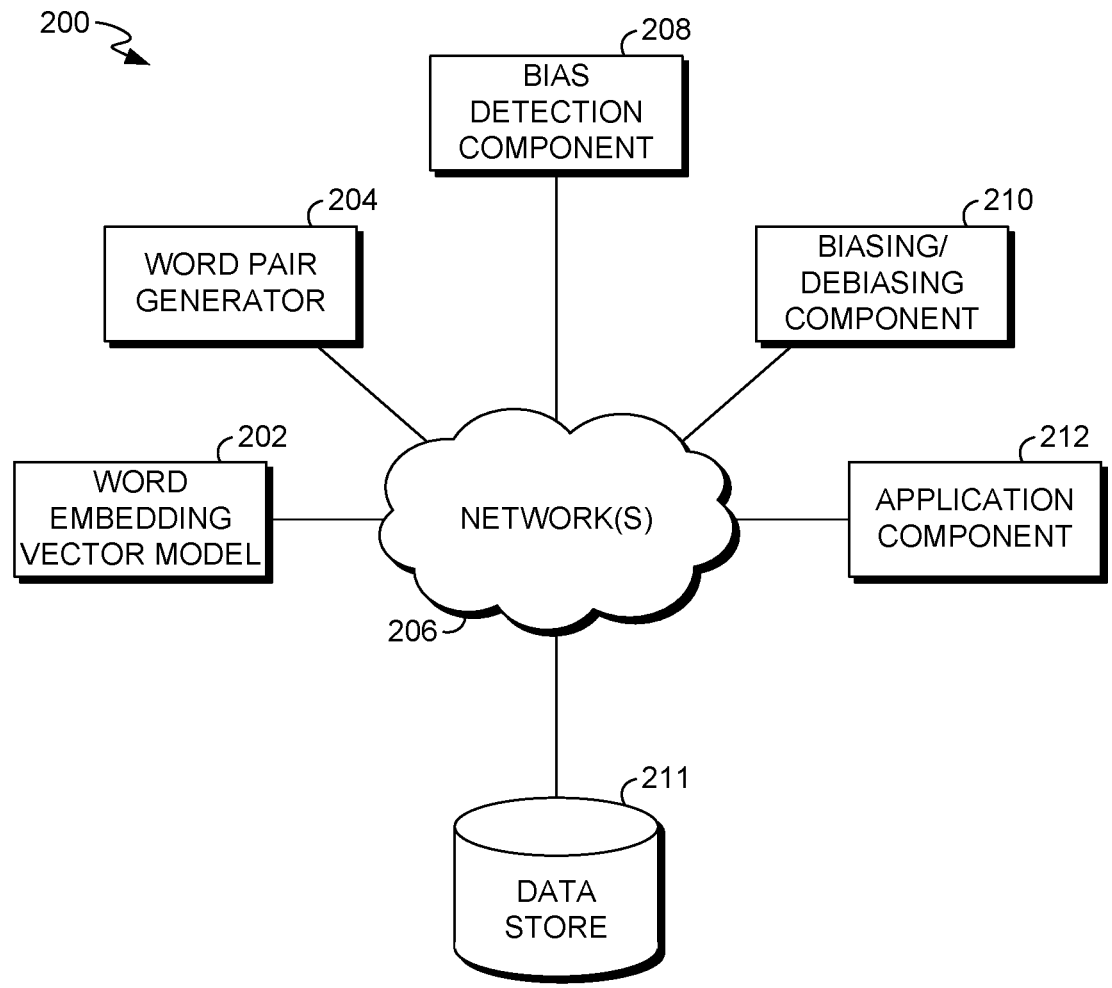
FIG. 2 is a block diagram of an example computing system for use in implementing some embodiments of the present invention.

Turning now to FIG. 2, an exemplary computing system 200 is depicted suitable for use in implementing embodiments of the present invention. The computing system 200 is merely an example of one suitable computing system environment and is not intended to suggest any limitation as to the scope of use or functionality of embodiments of the present invention. Neither should the computing system 200 be interpreted as having any dependency or requirement related to any single module/component or combination of modules/components illustrated therein. In some embodiments, some or each of the computing system 200's components are located within the server(s) 102 of FIG. 1. Alternatively or additionally, in some embodiments, some or each of the computing system 200's components are located within the one or more remote computers 108.

The computing system 200 includes the word embedding vector model 202, the word pair generator 204, the bias detection component 208, the biasing/de-biasing component 210, the one or more networks 206, and the data store 211.

The network(s) 240 may include, without limitation, one or more secure local area networks (LANs) or wide area networks (WANs). The network(s) 240 may be a secure network associated with a facility such as a healthcare facility. The secure network may require that a user log in and be authenticated in order to send and/or receive information over the network.

In some embodiments, one or more of the illustrated components/modules may be implemented as stand-alone applications. In other embodiments, one or more of the illustrated components/modules may be distributed across multiple consult engines or computing device hosts. The components/modules illustrated in FIG. 2 are exemplary in nature and in number and should not be construed as limiting. Any number of components/modules may be employed to achieve the desired functionality within the scope of embodiments hereof.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The word embedding vector model 202 includes a word embedding as described herein. In some embodiments, a word embedding is represented as a unit vector $\vec{w} \in \mathbb{R}^d$, with $\|\vec{w}\|=1$, for each word (or character sequence) $w \in W$. In most cases, it can be assumed that there are neutral categories of words (e.g., treatment types) $N \subset W$ within the word embedding, such as ultrasound physical therapy treatment, which, by definition is not specific to any treatment category, such as geriatric, pediatric, etc. These words, which are described in more detail herein, are also referred to as "category-neutral" words. In order to understand the notation of some of the algorithms described herein, the size of a set S of vectors is denoted by $|S|$. A set of vector pairs may be described as $P \subset W \times W$.

In various instances, similarity between words $w_1$ and $w_2$ in word embeddings is measured by their inner products. $\vec{w}_1 \cdot \vec{w}_2$. For example, the statement mouse is more similar to gerbil than $\overrightarrow{\text{mouse}} \cdot \overrightarrow{\text{gerbil}} \geq \overrightarrow{\text{mouse}} \cdot \overrightarrow{\text{elephant}}$. For arbitrary vectors u and v we define:

$$\cos(u, v) = \frac{u \cdot v}{\|u\| \|v\|}.$$

This normalized similarity between vectors u and v written as cos because it is the cosine of the angle between the two vectors. Since words are normalized $\cos(\vec{w}_1, \vec{w}_2) = \vec{w}_1 \cdot \vec{w}_2$.

In particular embodiments, the word pair generator 204 receives the word embedding vector model 202 as input and generates word pairings, which are to be later tested for bias. In some embodiments, this includes taking a seed pair of words (a, b), determining a seed direction (a-b), and generating a pair of words x and y, such that a to x is as b is to y indicating an analogy. The seed pair of words are typically associated with a category of bias that is tested, such as drugs, treatments, price, etc. In an example illustration, the seed pair of words can be a brand drug and an equivalent generic drug. After determining the testing distance, the x and/or y words are generated, such as brand drug is to back pain as generic drug is to lower back pain. In some embodiments, all pairs of words x, y are scored by the following metric:

$$s_{(a,b)}(x, y) = \begin{cases} \cos(\vec{a} - \vec{b}, \vec{x} - \vec{y}), & \text{if} \|\vec{x} - \vec{y}\| \leq \delta \\ 0, & \text{otherwise} \end{cases}$$

Where $\delta$ is a threshold for similarity. This metric indicates that an analogy pair should be close to parallel to the seed direction while the two words are not too far apart in order to be semantically coherent. In some embodiments, the parameter $\delta$ sets the threshold for similarity, such as semantic similarity. In some embodiments, if word embeddings are normalized, this threshold corresponds to an angle $\leq \pi/3$ indicating that the two words are closer to each other than they are to the origin. Accordingly, the two words forming the analogy are significantly closer together than two random vectors. Given the word embedding and seed words, in some examples the top analogous pairs are extracted or outputted with the largest positive S(a, b)scores. Accordingly, the output of the word pair generator 204 is pairs of word pairs with scores over a threshold indicating semantically similar vectors. In some embodiments, the output is additionally or alternatively vector pairs that are equidistant (or substantially equidistant) from another corresponding vector. For example, the seed vector Brand A drug may be a particular directional distance from shoulder pain, and the same directional distance may be computed from seed vector representing Brand A's generic equivalent to arrive at a different vector, arm pain. Accordingly, the system may output this as brand A drug is to shoulder pain as the generic is to arm pain. Therefore, shoulder pain and arm pain are x and y respectively and are the outputs given the seed inputs.

In some embodiments, these analogy pairs are manually tested via subject matter experts (SMEs) to help determine if the analogy pairs conceivably reflect a bias. For example, an SME might be a doctor or other healthcare specialists that can identify whether the analogies reflect biases. In this way, word pairs that were generated via the word pair generator 204 can be removed via a feedback tool (not shown) in order to more finely tune the pairs. For example, a graphical user interface can contain a feedback tool that allows a clinician to select a button on a UI to remove pairings that were scored over a threshold if those pairings do not indicate a true bias. Alternatively or additionally, a machine learning model may be trained to further filter or help determine whether a bias exists. For example, a system can include a corpus of over 2 million documents including peer-reviewed journals, school books, articles, etc. in order to employ all of the knowledge an SME might have and make predictions of biases based on locating patterns and associations in the corpus of knowledge.

The bias detection component 208 quantifies the amount of bias and/or identifies the target category subspace (e.g., direction) that defines the bias or lack thereof. Geometrically, bias can be captured by a category subspace in the word embedding. In some embodiments, a "category subspace" corresponds to or defines at least two vectors (e.g., seed word pairs) that indicate a species of a category based on the input received by the word pair generator 204. In some examples, a category subspace B is defined by k orthogonal unit vectors $B=\{b1, \ldots, b_k\} \ldots$ Where k=1, the category subspace can be a direction. In some embodiments, the projection of a vector v onto B can by made by $$vB = \sum_{j=1}^{k}(v \cdot bj)bj.$$

There may be multiple category subspaces for the same category. In an illustrative example, for the category of "drug A", one category subspace may be vector "drug A" and its generic equivalent "generic A." Another category subspace or direction of the same category may be the formal name of drug A and a formal name of the generic equivalent. In some embodiments, the system captures multiple category subspaces for the same category and determines which category subspace (i.e., the target category subspace) contains the most or the "direction" of bias. This can be calculated via any suitable method. For example, multiple category subspaces or pairs of words can be aggregated for a same category. When several category subspaces are combined, the target subspace denoted as $g \in \mathbb{R}^d$ is captured in the word embedding. This target subspace helps to quantify biases in word embeddings. Identifying category subspace can be understood using the following notation. A subspace B is defined by k orthogonal unit vectors B={b1, ..., $b_k$} ⊂. In some embodiments, where k=1, the subspace is a direction. In some examples, the projection of a vector v onto B is denoted by $$vB = \sum_{j=1}^{k}(v \cdot bj)bj.$$

In some embodiments, identifying a target category subspace includes the following algorithm. The inputs are: word sets W, defining set $D_1, D_2, \ldots D_N \subset W$ as well as embedding $\{\vec{w} \in \mathbb{R}^d\}_{w \in W}$ and integer parameter k≤1. Let $$\mu_i := \sum_{\vec{w} \in D_i} \vec{w}/|D_i|$$

be the way to define sets. Let the bias subspace F be the first k rows of the SVD(C) where $$c := \sum_{i=1}^{n}\sum_{\vec{w} \in D_i}(\vec{w}-\mu_i)^\top(\vec{w}-\mu_i)/|D_i|$$

The output is identifying a target category subspace that captures the most bias or a threshold quantity of bias. For example, using the illustration above, the seed words Drug A and "generic A" may capture significantly more bias compared to the formal names of these drugs. Accordingly, these words may be used as the input for the biasing/de-biasing component 210. In some embodiments, a category subspace additionally or alternatively corresponds to two points or vectors of a particular category along an axis in vector space, as described in more detail below.

In some embodiments, the bias detection component 208 captures category-neutral words. "Category-neutral" words are words or other character sequences that are or should be identical or similar over a threshold score. For example, Brand A drug and its generic equivalent may be in a category-neutral drug category if they are identical in every respect, except for cost. Conversely, Brand A drug and its generic equivalent are not category-neutral words if they differ in other aspects such as effectiveness of treatment, how they are introduced to the body, side effect differences, etc. In some embodiments, the bias detection component 208 compares the distances between vector pairs output by the word pair generator 204, where a pair of words (e.g., the output pairs of the word pair generator 204) are of the same category (e.g., and the category contains the target subspace).

Distance alone is not always indicative of bias, which is why various embodiments identify category-neutral words. If a first seed vector is at a particular distance to a vector, but a second seed vector of the same category is at a difference distance, this indicates a bias. Conversely, if a first seed vector is a particular distance to a vector, and a second seed vector of the same category is at the same distance or distance inside of a threshold, this indicates non-bias or that a vector has not been biased enough. However, mere differences in vector scores alone do not always reflect a bias or lack thereof. For example, a generic drug may be further away from a health condition compared to a brand drug not necessarily because there is a bias, but because the generic drug may not be as beneficial in remedying the health condition compared to the brand drug. Accordingly, various embodiments of the present disclosure determine category-neutral words first before vectors are biased or de-biased.

Determining category-neutral words may occur via any suitable method. For example, the bias detection component 208 may receive a selection from a SME indicating that words are category neutral. Alternatively or additionally, computing systems may make this determination by comparing various attributes of various words and determining how equivalent they are. For example, a computing system may perform data mining or other machine learning techniques where there are millions or thousands of data sources, such as books, journals, etc. in order to determine, for example, how similar treatment A of kids is compared to treatment A of the elderly community. If there are differences over a threshold score, the computing system may flag the words as not category neutral. Conversely, if the differences do not surpass the threshold score, the computing system may flag the words as category-neutral.

The biasing/de-biasing component 210 introduces a bias between vectors and/or removes a bias between vectors. Based at least in part on a first vector's distance to a second vector relative to a third vector's distance to the second vector, the third vector can be moved to introduce or remove bias. For example, the third vector can be moved (e.g., scored) closer to the second vector such that the third vector is closer to the second vector relative to the first vector's distance to the second vector, which his indicative of introducing a bias between the third vector and the second vector. In an illustrative example, the vectors may correspond to acute versus chronic treatments for acute back pain. A particular clinician that treats acute back pain only (not chronic) because he or she is in a trauma unit may query a system to determine what the best treatment option for a person with the acute back pain is. Accordingly, the biasing/de-biasing component 210 may move the acute treatment vector closer to the chronic treatment vector so that the clinician only receives the acute treatment results.

In some embodiments, the biasing/de-biasing component 210 receives the outputs generated by the bias detection component 208 to introduce or remove bias from the vectors. For example, in response to receiving the distance computations between vectors and the target category subspace, the biasing/de-biasing component 2010 can responsively move vectors. In an example illustration, with respect to biasing, the biasing/de-biasing component 210 can set all category words to 0 in the category target subspace and then amplify words outside of the category target subspace (and/ or within the category subspace) to ensure that one or more vectors are at some predetermined factor distance away from one or more other vectors. For example, if a computer application was based on prioritizing natural remedies above drug remedies, the biasing/de-biasing component 210 may identify a pair of vectors that analogize Drug remedy A is to headache as natural remedy B is to sinus, where sinus is at a further distance from headache compared to drug remedy A even though they may both remedy headaches. Accordingly, the biasing/de-biasing component 210 may move natural remedy B closer to headache such that B is closer than drug remedy A to headache in order to bias results for this application based on amplifying the words outside of the category subspace and setting all category words to 0 in this subspace.

In some embodiments, the system can remove bias via the following algorithm, Additional inputs: words to neutralize $N \subset W$, family of equality sets $\varepsilon=\{E_1, E_2, \ldots, E_m\}$ where each $E_i \subseteq W$. For each word $w \in N$, let $\vec{w}$ be re-embedded to $\vec{w}:=(\vec{w}-\vec{w}_S)/|\vec{w}-\vec{w}_S|$. For each set $E \in \varepsilon$, let $$\mu_i := \sum_{\vec{w} \in B} w/|E|$$
$$v := \mu - \mu_B$$

For each $w \in E$, $$\vec{w} := v + \sqrt{1-\|v\|^2} \frac{\vec{w}_B - \mu_B}{\|\vec{w}_B - \mu_B\|}.$$

Finally, output the subspace B and the new embedding $\{\vec{w} \in \mathbb{R}^d\}_{w \in W}$.

In some embodiments, biasing and/or de-biasing includes centering, scaling, or normalizing data (e.g., via Z-score normalization) inside the category target subspace and/or outside of the category target subspace. In this way, the vectors that are not moved (or moved) for biasing/de-biasing maintain its usefulness to explain relationships. For example, a first vector can be biased towards a second vector by a factor of N. However, other vectors may have to be re-scaled to maintain its usefulness for indicating relationships, such as scaling or moving each other vector by a factor of N−1 (or other N factor) in direction X. In this way, appropriate analogies can be maintained.

The application component 212 is a computing-based application uses the output from the components 202, 204, 208, and/or 210 to render information. For example, the application component 212 can be or include a search engine, a web application, and/or a locally installed app. In an illustrative example, the application component 212 is a web application that includes a user interface that a clinician uses to determine which appropriate remedies to use for particular symptoms or health conditions. In response to a query from the clinician, a result page can generate results using the word embedding vector model 202 that has been altered by the biasing/de-biasing component 210.

Figure 3A:
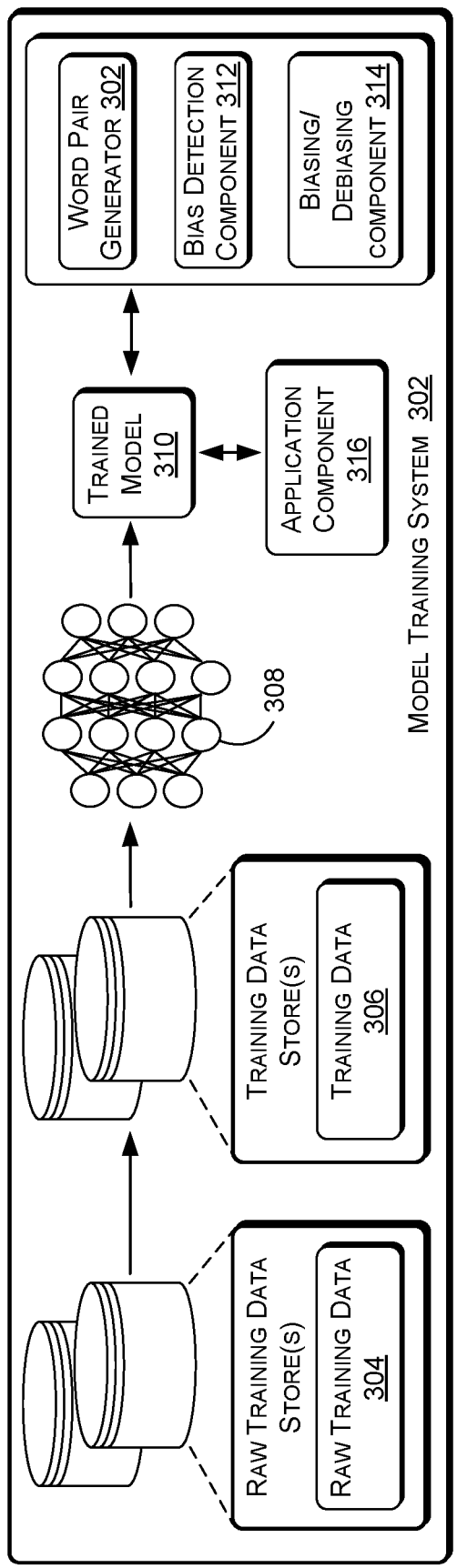
FIG. 3A is a schematic depiction is provided illustrating an example model training system for use in implementing some embodiments of the present invention.
Figure 3B:
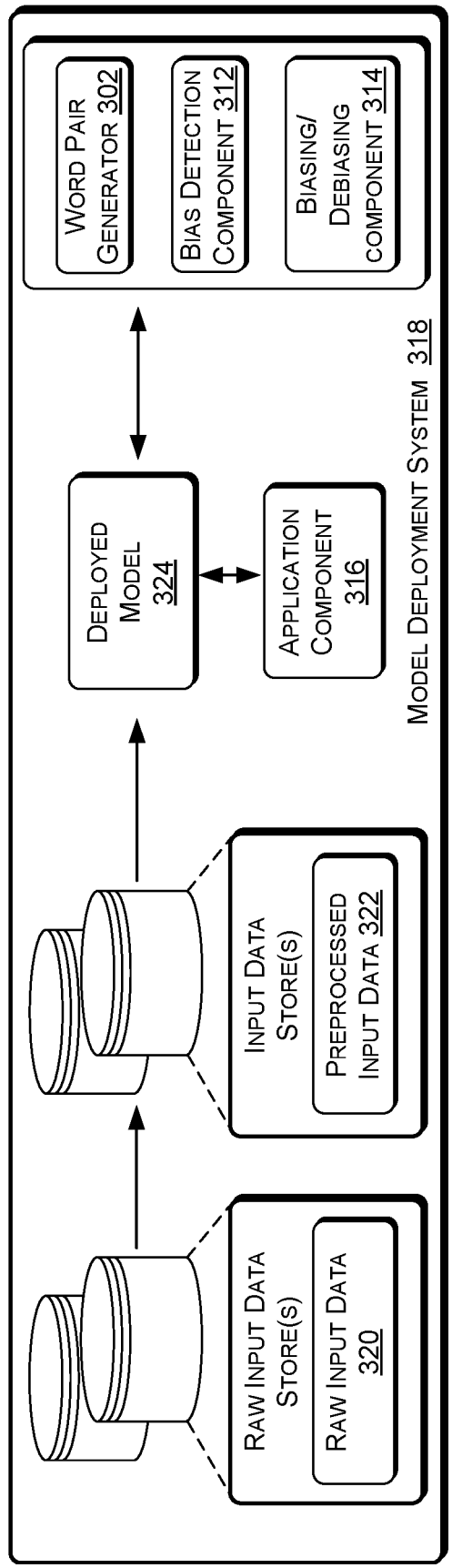
FIG. 3B is a schematic depiction is provided illustrating an example model deployment system for use in implementing some embodiments of the present invention.

With reference to FIG. 3A and FIG. 3B, reference to input data or data points may include raw training data 304, training data 306, raw input data 320, and/or preprocessed input data 322. Reference to output data may include data output by a trained model 310 (e.g., the word embedding vector model 202 of FIG. 2) and/or a deployed model 124 (e.g., the same word embedding vector model 202 of FIG. 2) used to classify the input data. Reference to performance may include the performance of the trained model 310 and/or the deployed model 324. The deployed model 324 may refer to the trained model 310 in a deployed environment of a computing system and/or application.

Referring now to FIG. 3A, a schematic depiction is provided illustrating an example model training system 302 in which some embodiments of the present disclosure may be employed. It should be understood that this and other arrangements described herein are set forth only as examples. Other arrangements and elements (e.g., machines, interfaces, functions, orders, groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by entities may be carried out by hardware, firmware, and/or software. For instance, various functions may be carried out by a processor executing instructions stored in memory.

The model training system 302 may include, among other things, a raw training data store(s) including raw training data 304, a training data store(s) including training data (e.g., after preprocessing the raw training data 304), a training component 308, a trained model 310, a word pair generator 302, a bias detection component 312, a biasing/de-biasing component 314, and an application component 316. The model training system 302 (and the components and/or features thereof) may be implemented using one or more computing devices, such as the one or more servers 102 of FIG. 1. In some embodiments, the word pair generator 302, the bias detection component 312, the biasing/de-biasing component 314, and the application component 310 is the same or performs the same functionality as the respective components described with respect to FIG. 2.

The raw training data 304 may include any type of raw data that may be used by the training component 308 to generate the trained model 310. The raw training data 304 may be collected, generated, and/or obtained from any number of sources, such as files, databases, data stores, sensors, and/or other sources of structured, semi-structured, or non-structured data. In some examples, the raw training data 304 may be used directly by the training component 308 (e.g., without preprocessing), such as when the training component 308 is training a 2-layer neural network that outputs a word embedding. In such examples, the training data store(s) and the accompanying training data 306 may not be included in the model training system 302. In some examples, a combination of the raw training data 304 and the training data 306 may be used by the training component 308 to generate the trained model 310. In other examples, the training component 308 may only use the training data 306 for generating the trained model 310. In other words, the raw training data 304, the training data 306, or a combination thereof may be used by the training component 308 to generate the trained model 310.

The training data 306 may include the raw training data 304 after preprocessing. For example, data preprocessing may be performed by the model training system 302 to convert the raw training data 304 into a clean (e.g., useable) data set (e.g., the training data 306). For example, the raw training data 304 may be collected, generated, and/or obtained in a raw format, which may not be feasible, effective, or usable by the training component 308 for generating the trained model 310. In addition, the raw training data 304 may include inaccurate or missing data (e.g., as a result of gaps in data collection, mistakes in data entries, technical problems with sensors, such as biometric sensors, and the like), noisy data (e.g., erroneous data or outliers), and/or inconsistent data (e.g., duplication of data, human data entry errors, mistakes in codes, etc.).

During preprocessing, the raw training data 304 may undergo various processes, such as data cleaning, data integration, data transformation, data reduction, and/or the like. For example, when the raw training data 304 includes inaccurate or missing data, the rows with missing data may be ignored (or deleted) when generating the training data 306 (in examples where the number of missing values is not too large), the missing data may be manually filled (in examples where the number of missing values is not too large to create an unreasonable task), and/or the missing values may be filled using computed values. For examples, to fill the missing values using computed values, the mean, mode, or median of the existing raw training data 304 could be used in place of the missing values. As another example, a machine learning model can be implemented to generate predictive values for the missing values of the raw training data 304.

When the raw training data 304 includes noisy data, the data preprocessing may include data binning, clustering, employing a machine learning model, and/or manual removal. For example, substantially continuous data from the raw training data 304 can be grouped together into a smaller number of "bins" (e.g., if the raw training data 304 includes every age from 0-100, the ages may be "binned" into groups of ages at five year intervals). As another example, similar data may be grouped together (e.g., into the same cluster or class), and/or a machine learning model (such as a regression algorithm) may be used to smooth the raw training data 304. In some examples, the noisy data can be deleted manually.

In some examples, after preprocessing, the raw training data 304 (and/or the training data 306) may undergo data wrangling (or data munging). For example, the training component 308 may use data wrangling during the training process of generating the trained model 310. Data wrangling may be used to transform and/or map the raw training data 304 into a different format that is more appropriate and/or valuable for downstream purposes (e.g., analytics). For example, as the training component 308 is training the model (e.g., after one or more iterations), a different format for the one or more types of the raw training data 304 (and/or training data 306) may be determined to be more suitable for downstream purposes than the format that is currently being used. By reformatting the raw training data 304 (and/or the training data 306), analysis of the input data, output data, and/or performance of the trained model 310 (and/or the deployed model 324 of FIG. 3B) may be more effective. In an example illustration, a natural language word can be changed to a real number (e.g., 0 or 1) to be represented as a feature value in vector space.

The training component 308 may use the raw training data 304 and/or the training data 306 to generate the trained model 310. Although the training component 308 of FIG. 3A includes a general illustration of a neural network, this is not intended to be limiting. For example, the training component 308 may be used to train any type of machine learning model, such as machine learning models using linear regression, logistic regression, decision trees, support vector machine (SVM), Naïve Bayes, k-nearest neighbor (Knn), K means clustering, random forest, dimensionality reduction algorithms, gradient boosting algorithms, neural networks (e.g., auto-encoders, convolutional, recurrent, perceptrons, long/short terms memory, Hopfield, Boltzmann, deep belief, deconvolutional, generative adversarial, liquid state machine, etc.), and/or other types of machine learning models.

The trained model 310 may be generated by the training component 308 using the raw training data 304 and/or the training data 306. The trained model 310 may include one or more models, such as word embedding vector models. Once it is determined that the trained model 310 has acceptable accuracy, the trained model 310 may be deployed (e.g., as the deployed model 324). The determination that a trained model 310 has acceptable accuracy or confidence may include a threshold accuracy, such as, for example and without limitation, 80%, 90%, 98%, etc. The threshold accuracy may be predefined by the model training system 302, or may be user defined.

In some embodiments, the training by the training component 308 includes changing an embedding or orientation of one or more vectors in feature space. In some embodiments, the training includes learning an embedding (e.g., a precise coordinate or position) of one or more vectors. Learning an embedding may include learning the distance between two or more vectors based on feature similarity of values between the vectors. For example, after a first round or set of rounds of training, it may be unknown which of the extracted features are important for taking on a certain embedding position. Accordingly, each feature may take on equal weight (or close to equal weight within a threshold, such as a 2% changed weight) such that all of the vectors are substantially close or within a distance threshold in feature space. However, after several rounds of training or any threshold quantity of training, these same feature vectors may adjust or change distances from each other based on the feature value similarity. The more features of two vectors that match or are within a threshold value, the closer the two vectors are to each other, whereas when features do not match or are not within a threshold value, the further away the two vectors are from each other.

The trained model 310 may be analyzed during training, after training, and/or after deployment (e.g., as the deployed model 324 of FIG. 3B) to evaluate the behavior of the trained model 310 by the word pair generator 302, the bias detection component 312, the biasing/de-biasing component 314 and/or the application component 316. For example, the bias/de-bias component 208 can bias vectors within the trained model 310 so as to move vectors in vector space and the application component can responsively generate results based on the tuned trained model 310. In this way the trained model 310 can be tuned outside of a training context via 304 and 306 in terms of biasing or de-biasing vectors.

Referring now to FIG. 3B, a schematic depiction is provided illustrating an example model deployment system 318 in which some embodiments of the present disclosure may be employed. It should be understood that this and other arrangements described herein are set forth only as examples. Other arrangements and elements (e.g., machines, interfaces, functions, orders, groupings of functions, etc.) can be used in addition to or instead of those shown, and some elements may be omitted altogether. Further, many of the elements described herein are functional entities that may be implemented as discrete or distributed components or in conjunction with other components, and in any suitable combination and location. Various functions described herein as being performed by entities may be carried out by hardware, firmware, and/or software. For instance, various functions may be carried out by a processor executing instructions stored in memory.

The model deployment system 318 may include, among other things, a raw input data store(s) including raw input data 320, an input data store(s) including preprocessed input data 322 (e.g., after preprocessing the raw input data 320), the deployed model 324, the word pair generator 302, the bias detection component 312, the biasing/de-biasing component 314, and the application component 316. Although these components are labeled with the same reference number in both FIG. 3A and FIG. 3B, this is not intended to be limiting. In some examples, the model training system 302 and the model deployment system 318 may include separate or distinct components. In addition, as described herein, in some examples the trained model 310 may be the same as the deployed model 324, while in other examples, the trained model 310 may be used to generate the deployed model 324. The model deployment system 318 (and the components and/or features thereof) may be implemented using one or more computing devices, such as the one or more servers 102 of FIG. 1.

As mentioned above, the deployed model 324 may correspond to the trained model 310 after the trained model 310 has been deployed in a computing system and/or application. In particular, classifications or predictions made using the deployed model 324 may be used to power downstream applications and/or services (e.g., the application component 316).

The raw input data 320 may be similar to the raw training data 304, except that the raw input data 320 is input into the deployed model 324. For example, the raw input data 320 may include any type of raw data that may be input into the deployed model 324 to generate output data. The raw input data 320 may be collected, generated, and/or obtained from any number of sources, such as files, databases, data stores, sensors, and/or other sources. In some examples, the raw input data 320 may be used directly by the deployed model 324 (e.g., with no or minimal preprocessing), such as when the deployed model 324 is a neural network for use in word embeddings. In such examples, the input data store(s) and the accompanying preprocessed input data 322 may not be included in the model deployment system 318. In some examples, a combination of the raw input data 320 and the preprocessed input data 322 may be used by the deployed model 324 to generate the output data. In other examples, the deployed model 324 may only use the preprocessed input data 322 for generating the output data. In other words, the raw input data 320, the preprocessed input data 322, or a combination thereof may be used by the deployed model 324 to generate the output data.

The preprocessed input data 322 may include the raw input data 320 after preprocessing. For example, similar to described above with respect to the raw training data 304 of the model training system 302 of FIG. 3A, data preprocessing may be performed by the model deployment system 318 to convert the raw input data 320 into a clean (e.g., useable) data set (e.g., the preprocessed input data 322).

In some examples, after preprocessing, and similar to the raw training data 304 (and/or the training data 306) of the model training system 302 of FIG. 3A described above, the raw input data 320 (and/or the preprocessed input data 322) may undergo data wrangling (or data munging).

The deployed model 324 may be generated, at least in part, by the training component 308 of the model training system 302 using the raw training data 304 and/or the training data 306. As described above, the deployed model 324 may be the trained model 310, may be one of the trained models 310 (e.g., where A/B testing was performed), and/or may be the trained model 310 after additional accuracy checking, retraining, in-deployment training (e.g., continuous training during deployment), and/or the like. The trained model 310 may include one or more models, such A/B models that are tested.

The deployed model 324 may be analyzed by the word pair generator 302, the bias detection component 312, the biasing/de-biasing component 314, and/or the application component 316. The performance metrics of the deployed model 324 may be calculated similarly to the performance metrics of the trained model 310, described herein. In addition, by scoring performance metrics of the trained model 110 to performance metrics of the deployed model 324, the model deployment system 318 may automatically identify performance anomalies of the deployed model 324. For example, during deployment the deployed model 324 could receive additional updates or training and it may be desirable to ensure that the model still performs like the model did prior to deployment, in one or more respects.

Figure 4A:
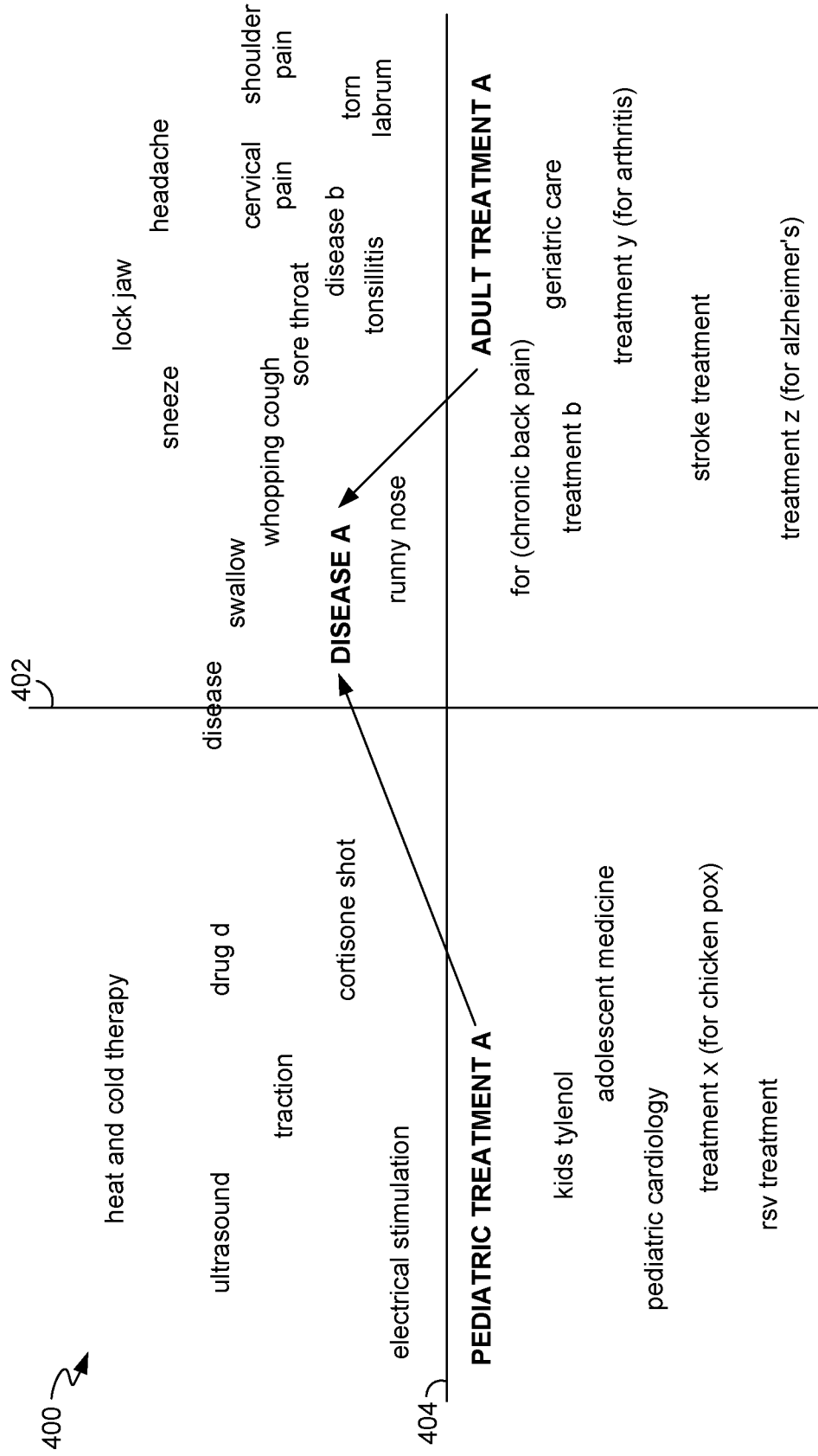
FIG. 4A is a schematic diagram illustrating how vectors associated with words are run through a word embedding vector model that outputs a word embedding, according to particular embodiments of the present invention.

FIG. 4A is a schematic diagram illustrating how vectors associated with words are run through a word embedding vector model that outputs a word embedding, according to some embodiments. In some embodiments, functionality described with respect to FIGS. 4A, 4B, 5A, and 5B represent the word embedding vector model 202 of FIG. 2, the trained model 310 of FIG. 3A, and/or the deployed model 324 of FIG. 3B. The vector space 400 includes multiple vectors (e.g., "runny nose", "disease A", etc.) illustrated in natural language text for convenience but are typically represented as vectors. It is understood that although the vector space 400, 400-1, 500, and 500-1 are representative only and that any suitable vectors according to a particular application can be represented.

In some embodiments, the word embedding vector model is a Word2vec model. A word2vec model is a two-layer network model that runs one or more input vectors (e.g., which represent a message element) through a hidden layer (i.e., a column-row matrix) and a projection layer (e.g., a softmax classifier). Word2vec models predict target strings from source context words (i.e., via the Continuous Bag of Words (CBOW) algorithm) or inversely predict source-context words from target words (i.e., via the skip-gram algorithm). In embodiments, when words are processed through a corresponding Word2vec or other word embedding model, the words are numerically represented in a word embedding that shows associated vectors and the distances from the string representations to each of those vectors, which is described in more detail below.

In order to plot data points or vectors within the vector space 400, the model is trained using training data (e.g., the training data 306). In various embodiments, the training data includes a large corpus of unstructured data (e.g., documents, news articles, social media posts, news feeds, blogs), semi-structured, and/or structured data (e.g., database values). The training data is also an input of the word embedding vector model. The training data includes some or each of the words as found within the vector space 400—sneeze, lockjaw, kids Tylenol, etc.

In some embodiments, the vector space 400 (and/or 500) represents a "pre-trained" embedding. A pre-trained embedding is a static model that is generated without feedback, retraining, or reference to the data sets being fed through it. For example, a user may download a static word embedding vector model from an online source, which is already trained and includes the vectors or data points already mapped in vector space according to semantic similarity between words. In other embodiments, the vector space 400 (and/or 500) represents a "retrained" or trained embedding. A retrained or trained word embedding model is an embedding that receives training feedback after it has received initial training session(s) and is optimized or generated for a specific data set (e.g., bias or remove bias from word embeddings).

In order to map each of the words to its contextually appropriate points in the vector space 509, training algorithms are utilized. For example, in some embodiments, the word embedding vector model is trained using the maximum likelihood (ML) principle to maximize probability of the next word $w_t$ (i.e., "target") given the previous words h (i.e., "history") in terms of a softmax function:

$$P(w_t|h) = \text{softmax}(\text{score}(w_t, h))$$

$$\exp\{\text{score}(w_t, h)\} = \underbrace{\qquad}_{(w', h)} \Sigma \text{word } w' \text{ in Vocab}^{exp\{score\}}$$

Where score ($w_t$, h) computes the compatibility of word $w_t$ with the context h. The model is trained by maximizing its log-likelihood on the training set, that is maximizing $$J_{ML} = \log P(w_t|h)$$
$$= \text{score}(w_t, h) - \log\left(\frac{\exp(\text{score}(w', h))}{\sum \text{Word } w' \text{ in Vocab}}\right)$$

This yields a properly normalized probabilistic model for language modeling. Each probability is computed and normalized using the score for all other words w' in the current context h at every training step. In some embodiments, some models, such as word2vec, are trained using a binary classification objective, such as logistic regression, to discriminate the real target words $w_t$ from K noise words w", in the same context. Accordingly, instead of a softmax classifier, a noise classifier is used.

The output of the training algorithms and/or actual data input is each of the positional words in the vector space 400 (and/or 500), which shows groupings of words that are similar (e.g., semantically similar). "Semantic similarity" is the semantic distance between two or more concepts (e.g., vectors representing healthcare terms). The "distance" between any two or more words in some embodiments is based on the similarity of their meaning and/or semantic content, as opposed to any syntax similarity. For example, "car" and "far" are syntactically similar but have two different definitions so they are not semantically similar.

In some embodiments, the output as represented in the vector space 400 (and/or 500) is plotted in response to the word embedding vector model receiving and plotting points. For example, a vocabulary set (e.g., all the words in the vector space 400) may first be converted into input vectors via an input vector encoding (e.g., one hot encoding). For example, the word "headache" may be converted into the vector [1,0,0,0,0]. This vector representation shows five dimensions (even though this FIG. 4A shows more dimensions) where each value corresponds to ordered words (e.g., each word in a sentence or vocabulary) in the message and whether the word is TRUE or present. Because "headache" is the only word being run through the word embedding vector model in this example, the integer 1 is used to indicate its representation. "Headache" does not contain any of the other words with it so the other values are represented as 0. In some embodiments, based on generating the softmax function above or the output layer of the neural network, an output embedding vector representation can be generated, which is indicative of the actual coordinates that a vector will be plotted in vector space 400 (and/or 500) based on semantic similarity to other words and/or averaging or otherwise combining the output embedding vectors for all of the words within the message vectors 400. For example, using the illustration above, the headache vector [1,0,0,0,0] can be converted to an output layer vector [1,2], which is the 2-dimensional plotting coordinates in vector space 400 (and/or 500).

The distance between any two vectors or words is measured according to any suitable method. For example, in some embodiments, automated cosine similarity is used to compute distance. Cosine similarity is a measure of similarity between two non-zero vectors of an inner product space that measures the cosine of the angle between the two non-zero vectors. In these embodiments, no similarity is expressed as a 90 degree angle, while total similarity (i.e., the same word) of 1 is a 0 degree angle. For example, a 0.98 distance between two words reflects a very high semantic similarity while a 0.003 distance reflects little semantic similarity. As illustrated in the vector space 500-1, for example, the cosine similarity between "generic drug A" and "swallow" and "brand name drug A" and "cough" are the same cosine distance, thus swallow in certain situations is semantically similar to cough given the inputs of generic drug A and Brand name drug A. In some embodiments, the distance is represented as an average distance or the distance between a particular vector in vector space 400 (and/or 500) and an average of query terms. In some embodiments, the distance is represented via fuzzy matching.

In some embodiments, FIG. 4 and FIG. 5 represent or includes a word-category co-occurrence matrix (e.g., a compilation of vector spaces). A matrix includes one or more vectors of a first vector space multiplied by one or more vectors of a second vector space. This allows rows within the vector space to be normalized for summing to 1 to become a probability distribution. Words or vectors can be compared using their category distribution.

After the training data is run through the training algorithm, the output is represented in FIG. 4A. In some embodiments, the vector space 400 is representative of how a word embedding appears after the bias detection component 208 performs its functionality. Accordingly, category-neutral words are separated from non-category neutral words and/or the direction or subspace of words between pediatric treatment A and adult treatment A have been generated. That is, the x-axis 404 defines the two words being tested at the opposites (e.g., in magnitude and distance)—pediatric treatment A and adult treatment A and the corresponding subspace. Every word below the X-axis 404 indicates words that are not category-neutral, such that they directly correlate to either pediatric treatment A or adult treatment A and typically do not cross over treatments even though data may indicate a bias. For example, the vector kids Tylenol will likely always be close to pediatric treatment A compared to adult treatment A because it is treatment-specific or specific to pediatric care and should never move or change positions. Accordingly, in various embodiments, words below the x-axis 404 may never be moved to introduce or remove bias even though they may appear to have a particular bias value because they are not category-neutral words. Conversely, every word above the X-axis 404 may indicate category-neutral words. For example, "ultrasound" may be a treatment used in both pediatric treatment A and adult treatment A. These vectors above the x-axis 404 are the words and subspace (e.g., direction) used to bias vectors. Particularly, the Y-axis 402 is a direction learned in the word embedding that captures category-neutral words.

Figure 4B:
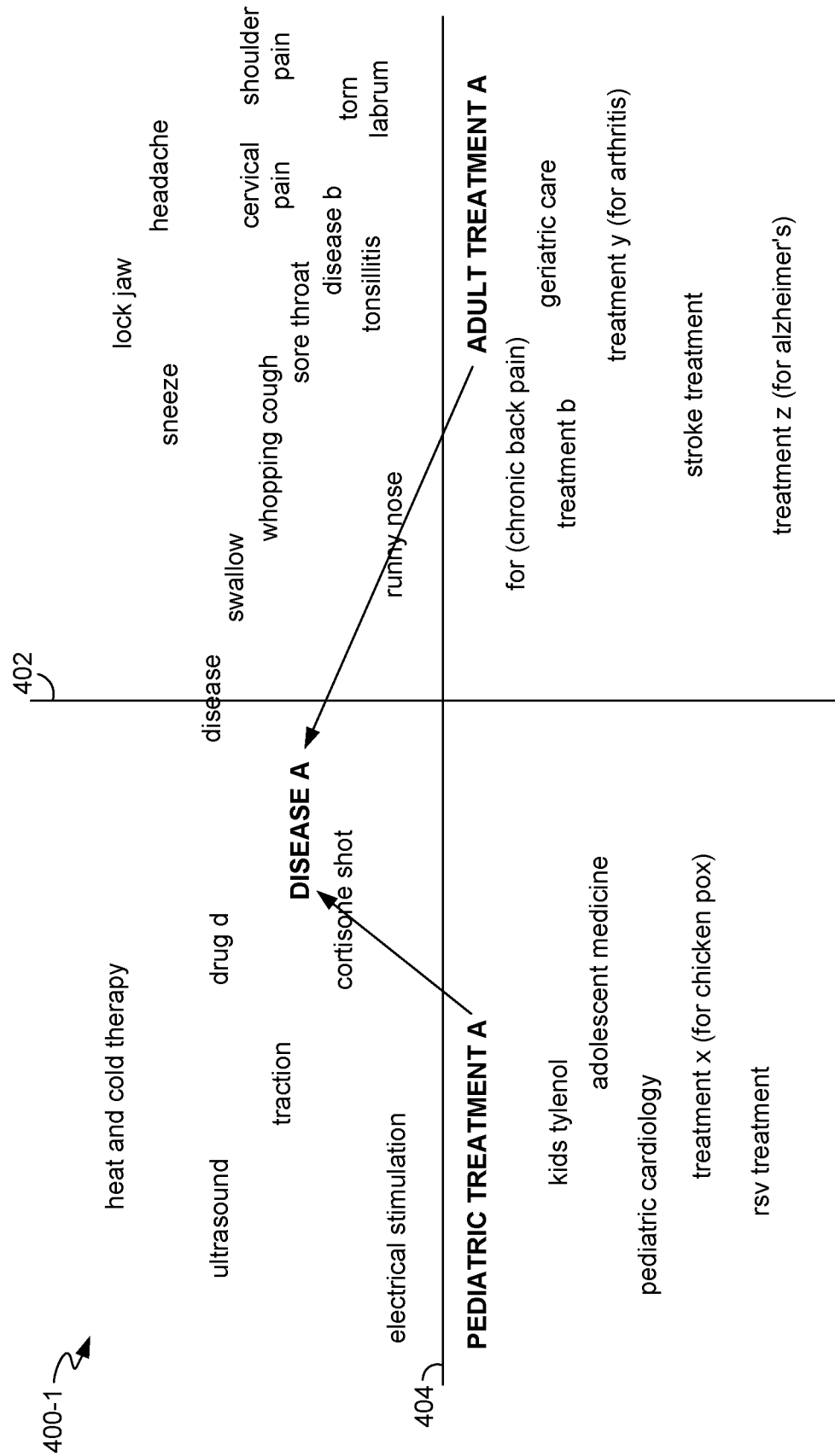
FIG. 4B is a schematic diagram illustrating how a vector of FIG. 4A is biased towards other vectors, according to particular embodiments of the present invention.

As illustrated and according to particular applications, there may not be enough bias for vector disease A, which may be a disease that mostly children get even though adults may contract the disease. Accordingly, as illustrated in FIG. 4B, the vector disease A is moved closer (e.g., in magnitude) to pediatric treatment A and is thus further away from adult treatment A. FIG. 4B is a schematic diagram illustrating how a vector of FIG. 4A is biased towards other vectors, according to some embodiments. In some embodiments, the moving in FIG. 4B is the output that the biasing/de-biasing component 210 generates.

Figure 4C:
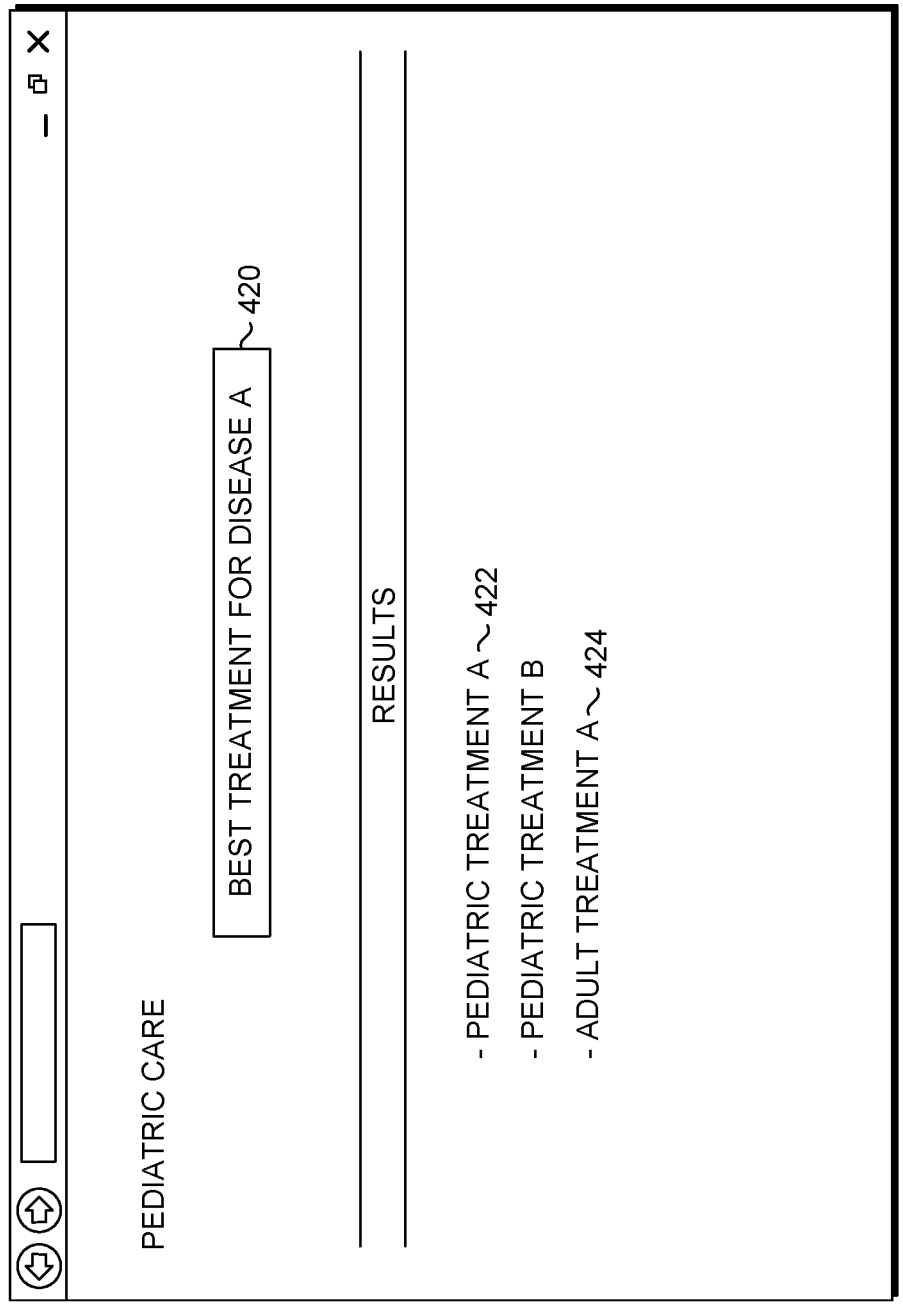
FIG. 4C is a screenshot of a graphical user interface that uses FIG. 4B as input, according to particular embodiments of the present invention.

FIG. 4C is a screenshot 400-3 of a graphical user interface that uses FIG. 4B as input to generate search results, according to particular embodiments. In response to the moving of the vector disease A closer to pediatric treatment A according to FIG. 4B, a model and associated word embedding can be deployed or otherwise usable for particular computer applications (e.g., application component 212), as illustrated in FIG. 4C. The screenshot 400-3 may correspond to a particular pediatric care web page, for example. Accordingly, any queries that users issue within the field 420 should render results that are pediatric-specific. As illustrated in FIG. 4C, when a user (e.g., a clinician or patient) issues the query "Best Treatment for Disease A", the system can execute the query, which includes running the query or terms in the query (e.g., "disease A") through a word embedding vector model that outputs the word embedding of FIG. 4B. Because "pediatric treatment A" is closer to "disease A" relative to "adult treatment A", pediatric treatment A search result 422 is output on a display page as a higher search result relative to adult treatment A search result 424 corresponding to adult treatment A. However, had "disease A" not been biased according to FIG. 4B (i.e., remained identical to FIG. 4A), then the search result 424 may have been ranked first or scored higher or closer relative to search result 422, which would be inaccurate.

FIG. 5A is a schematic diagram illustrating how vectors associated with words are run through a word embedding vector model that outputs a word embedding, according to some embodiments. In some embodiments, FIG. 5A can include the functionality as described with respect to FIG. 4A. FIG. 5A illustrates that an original word embedding in the vector space 500 indicates that "brand name drug A" is to "cough" as "generic drug A'" is to "swallow" (e.g., swallow is the same magnitude and direction from generic drug a as cough is to brand name drug A). In various instances this indicates a bias, since both drugs (brand name drug A and Generic drug A'), which may be identical in most respects and are used to both treat cough, are not the same distance (in magnitude and distance) away from cough. Rather, brand name drug A is closer to cough than generic drug A' is.

FIG. 5B is a schematic diagram illustrating how vectors are moved to remove the bias indicated in FIG. 5A, according to particular embodiments. Accordingly, generic drug A' can be moved at the same coordinates as brand name drug A such that both of these vectors are equidistant to cough. In some embodiments, the moving is in both magnitude and direction to arrive at equidistant values. Alternatively, in some embodiments, the moving includes moving in magnitude or direction but not both.

FIG. 5C is a screenshot 500-3 of a graphical user interface that uses FIG. 5B as input to generate search results, according to particular embodiments. In response to the moving of the vector generic drug A at the same point in vector space 500-1 according to FIG. 5B, a model and associated word embedding can be deployed or otherwise usable for particular computer applications, as illustrated in FIG. 5C. The screenshot 500-3 may correspond to a particular medical application that renders remedy recommendations for particular health conditions, for example. Accordingly, any queries that users issue within the field 502 should render results that indicate a drug to use for specific health conditions. As illustrated in FIG. 5C, when a user (e.g., a clinician or patient) issues the query "which drugs are best to use for cough" in the field 502, the system can execute the query, which includes running the query or terms in the query (e.g., "drugs", "cough") through a word embedding vector model that outputs the word embedding of FIG. 5B. Because brand name drug A and generic drug A' are a same distance to cough, these vectors are output as natural language search result entries 504 and 506 on the results page with a score that is the same (0.92), indicating that they are both equidistant to cough. In various instances, had bias not been removed (i.e., the word embedding 500 of FIG. 5A was used), then "generic drug A" search result 504 may have had a lower score (e.g., 0.54) or may be ranked in a lower position on the search results page based on "generic drug A" being further away from "cough" relative to its position in FIG. 5A and/or being at a different distance and/or magnitude to cough relative to "brand name drug A."

FIG. 6 is a flow diagram of an example process 600 for introducing and/or removing bias between vectors, according to some embodiments. The process 600 (and/or any of the functionality described herein) may be performed by processing logic that comprises hardware (e.g., circuitry, dedicated logic, programmable logic, microcode, etc.), software (e.g., instructions run on a processor to perform hardware simulation), firmware, or a combination thereof. Although particular blocks described in this disclosure are referenced in a particular order at a particular quantity, it is understood that any block may occur substantially parallel with or before or after any other block. Further, more (or fewer) blocks may exist than illustrated. Such added blocks may include blocks that embody any functionality described herein. The computer-implemented method, the system (that includes at least one computing device having at least one processor and at least one computer readable storage medium), and/or the computer program product as described herein may perform or be caused to perform the processes 600 and/or any other functionality described herein.

Per block 602 a word embedding is received (e.g., by the word pair generator 204 or the server(s) 102). In various instances, the word embedding includes a plurality of vectors in vector space (e.g., the word embedding of FIG. 4A). In some embodiments, each vector of the plurality of vectors represents a natural language word or other character sequence. In particular embodiments, the each vector is oriented in the vector space based on a similarity (e.g., semantic similarity) between each of the natural language word or other character sequence (e.g., as indicated in FIG. 4A). In some embodiments, the natural language word represents a healthcare term and one or more search results are for use by a clinician or user using a healthcare information system (e.g., as indicated in FIGs. 4C and/or 5C). For example, the healthcare term can be drugs (e.g., brand and generics, treatments, or other medical terms described herein). In some embodiments, the word embedding is one or more of: Word2Vec, GloVe, fastText, Brown Clustering, Gensim.

Per block 604, a distance between a first vector and a second vector and between a third vector and the second vector is determined (e.g., by the bias detection component 208). Specifically and in some instances, a first distance between the first vector and the second vector is determined as well as a second distance between the third vector and second vector are determined. For example, referring back to FIG. 4A, a distance between pediatric treatment A and disease A is determined as well as a distance between adult treatment A and the same vector disease A. In various instances, it is determined that the first vector is closer, in vector space, to the second vector relative to the third vector's distance to the second vector. This may indicate a need to introduce bias. For example, referring back to FIG. 4A, it is determined that disease A is closer to adult treatment A than pediatric treatment A, indicating a need to bias disease A closer to pediatric treatment A. In some embodiments, the same vector space can also contain vectors that additionally need to have bias removed or de-biased. For example, it can be determined that a fourth vector is closer, in the vector space, to a fifth vector relative to a sixth vector's distance to the fifth vector. In an illustrative example, referring back to FIG. 5A, it can be determined that brand name drug A is closer to cough relative to generic drug A's distance to cough. However, these vectors might be category-neutral and should not reflect unequal distances to the fifth vector so there should not be a bias.

In some embodiments, the determining is block 604 is preceded or followed by determining which words are category-neutral words (and/or not category-neutral) in the word embedding and/or determining a target category subspace, as described with respect to the bias detection component 208 and FIG. 4A. For example, referring back to FIG. 4A, each category-neutral word is placed above the x-axis 404 while each non-category-neutral word is placed below the x-axis, a direction or subspace is defined between the pediatric treatment A and adult treatment a, which includes making these vectors opposite ends of the x-axis 404. The identified subspace, of the vector space, captures the bias or lack of bias between vectors, particularly above the x-axis 404.

Per block 606, the third vector is moved (e.g., by the biasing/de-biasing component 210) closer to the second vector or the third vector is moved further away from the second vector. The moving is indicative of introducing bias or removing a bias in the word embedding. For example, based at least in part on the first vector being closer to the second vector relative to the third vector's distance to the second vector, the third vector is moved closer to the second vector such that the third vector is closer to the second vector relative to the first vector's distance to the second vector. In various embodiments, this moving is indicative of introducing a bias between the third vector and the second vector. In an illustrative example, referring back to FIG. 4B, disease A is moved closer to pediatric treatment A based on adult treatment being closer to disease A in FIG. 4A.

Alternatively or additionally, the moving can include removing a bias. For example, based at least in part on the first distance between the first vector and the second vector and the second distance between the third vector and the second vector, the third vector can be moved closer or further from the second vector to remove the bias. For example, referring back to FIG. 5B, generic drug A can be moved closer to cough such that brand name drug A is the same distance from cough compared to generic drug A's distance to cough, which removes the bias.

In some embodiments, the moving of the third vector is based at least in part on the identifying of the subspace and/or generating category-neutral words. For example, referring back to FIG. 4A, only after category-neutral words are indicated above the x-axis 404 and the subspace has been defined between pediatric treatment A and adult treatment A, can distance be determined and vectors moved.

In some embodiments, as described with respect to the fourth, fifth, and sixth vectors above, based at least in part on the fourth vector being closer to the fifth vector relative to the sixth vector's distance to the fifth vector, the sixth vector is moved closer to the fifth vector such that the sixth vector and the fifth vector are substantially at a same distance to the fourth vector. This moving is indicative of de-biasing the fifth vector and the sixth vector. An example of this is illustrated in FIG. 5B where generic drug A' is been moved at or near brand name drug A such that these vectors are at a same distance to cough.

In some embodiments, the introducing of the bias is indicative of shifting a healthcare term to favor a cheap generic drug over a branded drug or shifting the healthcare term to favor a pediatric treatment over an adult treatment. For example, referring back to FIG. 4B, the healthcare term disease A is shifted closer to pediatric treatment A such that pediatric treatments will ranked higher in computing applications relative to adult treatments.

In some embodiments, the moving of the third vector includes changing a magnitude and/or direction of placement of the third vector in the vector space. For example, referring back to FIG. 5B, generic drug A has shifted further down the y-axis in magnitude and further towards the origin according to the x-axis, indicating a change in magnitude and direction.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

Having described embodiments of the present invention, an exemplary operating environment in which embodiments of the present invention may be implemented is described below in order to provide a general context for various aspects of the present invention. Referring initially to FIG. 7 in particular, an exemplary operating environment for implementing embodiments of the present invention is shown and designated generally as computing device 700. Computing device 700 is but one example of a suitable computing environment and is not intended to suggest any limitation as to the scope of use or functionality of the invention. Neither should the computing device 700 be interpreted as having any dependency or requirement relating to any one or combination of components illustrated.

Looking now to FIG. 7, computing device 700 includes a bus 710 that directly or indirectly couples the following devices: memory 712, one or more processors 714, one or more presentation components 716, input/output (I/O) ports 718, input/output components 720, and an illustrative power supply 722. Bus 710 represents what may be one or more busses (such as an address bus, data bus, or combination thereof). Although the various blocks of FIG. 7 are shown with lines for the sake of clarity, in reality, delineating various components is not so clear, and metaphorically, the lines would more accurately be grey and fuzzy. For example, one may consider a presentation component such as a display device to be an I/O component. Also, processors have memory. The inventor recognizes that such is the nature of the art, and reiterates that the diagram of FIG. 7 is merely illustrative of an exemplary computing device that can be used in connection with one or more embodiments of the present invention. Distinction is not made between such categories as "workstation," "server," "laptop," "hand-held device," etc., as all are contemplated within the scope of FIG. 7 and reference to "computing device."

Computing device 700 typically includes a variety of computer-readable media. Computer-readable media can be any available media that can be accessed by computing device 700 and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computing device 700. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

In various embodiments, the computing device 700 represents the remote computers 108 and/or the one or more servers 102 and vice versa.

Memory 712 includes computer-storage media in the form of volatile and/or nonvolatile memory. The memory may be removable, non-removable, or a combination thereof. Exemplary hardware devices include solid-state memory, hard drives, optical-disc drives, etc. Computing device 700 includes one or more processors that read data from various entities such as memory 712 or I/O components 720. Presentation component(s) 716 present data indications to a user or other device. Exemplary presentation components include a display device, speaker, printing component, vibrating component, etc. In some embodiments, the memory includes program instructions that, when executed by one or more processors, cause the one or more processors to perform any functionality described herein, such as the process 600 of FIG. 6.

I/O ports 718 allow computing device 700 to be logically coupled to other devices including I/O components 720, some of which may be built in. Illustrative components include a microphone, joystick, game pad, satellite dish, scanner, printer, wireless device, etc. The I/O components 720 may provide a natural user interface (NUI) that processes air gestures, voice, or other physiological inputs generated by a user. In some instances, inputs may be transmitted to an appropriate network element for further processing. An NUI may implement any combination of speech recognition, stylus recognition, facial recognition, biometric recognition, gesture recognition both on screen and adjacent to the screen, air gestures, head and eye tracking, and touch recognition (as described in more detail below) associated with a display of the computing device 700. The computing device 700 may be equipped with depth cameras, such as stereoscopic camera systems, infrared camera systems, RGB camera systems, touchscreen technology, and combinations of these, for gesture detection and recognition. Additionally, the computing device 700 may be equipped with accelerometers or gyroscopes that enable detection of motion. The output of the accelerometers or gyroscopes may be provided to the display of the computing device 700 to render immersive augmented reality or virtual reality.

As can be understood, embodiments of the present invention provide for, among other things, generating proof and attestation service notifications corresponding to a determined veracity of a claim. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and sub combinations are of utility and may be employed without reference to other features and sub combinations. This is contemplated by and is within the scope of the claims.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

What is claimed is:
1. A computer-implemented method comprising:
receiving a word embedding, the word embedding including a plurality of vectors in vector space, each vector of the plurality of vectors represents a natural language word or other character sequence, the each vector being oriented in the vector space based on a similarity between each of the natural language word or other character sequence;

determining that a first set of vectors, in the vector space, are category-neutral, each vector that is category-neutral being similar over a threshold and not belonging to any one specific category;

in response to the determining, determining that a target category subspace, among a plurality of category subspaces, indicates a quantity of bias below a threshold, the set of vectors that are category-neutral being included in one or more category subspaces of the plurality of category subspaces, the plurality of category subspaces being included in the vector space;

based at least in part on the determining that the target category subspace indicates a quantity of bias below a threshold, moving a third vector closer to a second vector such that the third vector is closer to the second vector relative to a first vector's distance to the second vector, the moving being indicative of introducing a bias between the third vector and the second vector;

receiving, at a search engine, a query to access one or more resources; and based at least in part on the moving, causing display of one or more search results to execute the query.

2. The method of claim 1, wherein the natural language word represents a healthcare term, and wherein the one or more search results are for use by a clinician or user using a healthcare information system.

3. The method of claim 2, wherein the introducing of the second bias is indicative of shifting the healthcare term to favor a cheap generic drug over a branded drug or shifting the healthcare term to favor a pediatric treatment over an adult treatment.

4. The method of claim 1, further comprising:

determining that a fourth vector is closer, in the vector space, to a fifth vector relative to a sixth vector's distance to the fifth vector, wherein the fourth vector, the fifth vector, and the sixth vector are included in the plurality of vectors; and based at least in part on the fourth vector being closer to the fifth vector relative to the sixth vector's distance to the fifth vector, the fourth and fifth vector being category-neutral and the determining that the target category subspace indicates a lowest quantity of bias, moving the sixth vector closer to the fifth vector such that the sixth vector and the fifth vector are substantially at a same distance to the fourth vector, the moving being indicative of de-biasing the fifth vector and the sixth vector, wherein the fourth vector, the fifth vector, and the sixth vector are all located in the target category subspace.

5. The method of claim 4, further comprising, prior to the moving of the sixth vector closer to the fifth vector, determining a direction of bias associated with the sixth vector.

6. The method of claim 1, wherein the moving of the third vector closer to the second vector such that the third vector is closer to the second vector relative to the first vector's distance to the second vector includes changing a magnitude and direction of placement of the third vector in the vector space.

7. The method of claim 1, wherein the word embedding is one word embedding of a group of word embeddings consisting of: Word2Vec, GloVe, fast Text, Brown Clustering, and Genism.

8. One or more computer storage media having computer-executable instructions embodied thereon that, when executed, by one or more processors, cause the one or more processors to perform a method, the method comprising:

receiving a word embedding, the word embedding including a plurality of vectors in vector space, each vector of the plurality of vectors represents a natural language word or other character sequence, the each vector being oriented in the vector space based on a similarity between the plurality of vectors;

determining that a first set of vectors, in the vector space, are category-neutral, and that a second set of vectors, in the vector space, are not category-neutral, each vector that is category-neutral being similar over a threshold and not belonging to any one specific category, in response to the determining, determining that a target category subspace, among a plurality of category subspaces, indicates a highest or lowest quantity of bias, the first set of vectors that are category-neutral being included in one or more category subspaces of the plurality of category subspaces;

in response to the determining that the target category subspace indicates the highest or lowest quantity of bias, determining a first distance between a first vector and a second vector and determining a second distance between a third vector and the second vector, wherein the first vector, the second vector, and the third vector are included in the target category subspace; and based at least in part on the first distance between the first vector and the second vector and the second distance between the third vector and the second vector, moving the third vector closer to the second vector or moving the third vector further away from the second vector, the moving being indicative of introducing a bias between the third vector and the second vector or removing the bias between the third vector and the second vector.

9. The one or more computer storage media of claim 8, wherein the natural language word represents a healthcare term, and wherein the one or more search results are for use by a clinician or user using a healthcare information system.

10. The one or more computer storage media of claim 8, wherein the introducing of the second bias is indicative of shifting a healthcare term to favor a cheap generic drug over a branded drug or shifting the healthcare term to favor a pediatric treatment over an adult treatment.

11. The one or more computer storage media of claim 8, the method further comprising:

determining that a fourth vector is closer, in the vector space, to a fifth vector relative to a sixth vector's distance to the fifth vector, wherein the fourth vector, the fifth vector, and the sixth vector are included in the plurality of vectors; and based at least in part on the fourth vector being closer to the fifth vector relative to the sixth vector's distance to the fifth vector, moving the sixth vector closer to the fifth vector such that the sixth vector and the fifth vector are substantially at a same distance to the fourth vector, the moving being indicative of de-biasing the fifth vector and the sixth vector.

12. The one or more computer storage media of claim 11, the method further comprising, prior to the moving of the sixth vector closer to the fifth vector, determining a direction of bias associated with the sixth vector.

13. The one or more computer storage media of claim 8, wherein the moving of the third vector closer to the second vector such that the third vector is closer to the second vector relative to the first vector's distance to the second vector includes changing a magnitude and direction of placement of the third vector in the vector space.

14. The one or more computer storage media of claim 8, wherein the word embedding is one word embedding of a group of word embeddings consisting of: Word2Vec, GloVe, fast Text, Brown Clustering, and Genism.

15. A system comprising:
one or more processors; and
one or more computer storage media storing computer-useable instructions that, when used by the one or more processors, cause the one or more processors to perform a method, the method comprising:
receiving a word embedding, the word embedding including a plurality of vectors in vector space, each vector of the plurality of vectors represents a natural language word or other character sequence, the each vector being oriented in the vector space based on a similarity between each of the natural language word or other character sequence, the natural language word or other character sequence representing a word in a healthcare information system;
determining that a first set of vectors, in the vector space, are category-neutral, and that a second set of vectors, in the vector space, are not category-neutral, each vector that is category-neutral being similar over a threshold and not belonging to any one specific healthcare category;
in response to the determining, identifying a target category subspace, of the vector space, that captures a first bias or lack of bias between a first vector and at least a second vector of the first set of vectors;
in response to the identifying of the target category subspace, quantifying the first bias or lack of bias between the first vector and at least the second vector of the plurality of vectors; and
based at least in part on the identifying of the target category subspace, moving the first vector closer to at least the second vector or moving the first vector further away from at least the second vector, the moving being indicative of introducing a second bias between the first vector and the second vector or removing the first bias between the first vector and at least the second vector.

16. The system of claim 15, wherein the natural language word represents a healthcare term, and wherein the one or more search results are for use by a clinician or user using a healthcare information system.

17. The system of claim 15, wherein the introducing of the second bias is indicative of shifting the healthcare term to favor a cheap generic drug over a branded drug or shifting the healthcare term to favor a pediatric treatment over an adult treatment.

18. The system of claim 15, the method further comprising:
determining that a fourth vector is closer, in the vector space, to a fifth vector relative to a sixth vector's distance to the fifth vector, wherein the fourth vector, the fifth vector, and the sixth vector are included in the plurality of vectors; and
based at least in part on the fourth vector being closer to the fifth vector relative to the sixth vector's distance to the fifth vector, moving the sixth vector closer to the fifth vector such that the sixth vector and the fifth vector are substantially at a same distance to the fourth vector, the moving being indicative of de-biasing the fifth vector and the sixth vector.

19. The system of claim 17, the further comprising, prior to the moving of the sixth vector closer to the fifth vector, determining a direction of bias associated with the sixth vector.

20. The system of claim 15, wherein the moving of the first vector closer includes changing a magnitude and direction of placement of the first vector in the vector space.

* * * * *